(12) United States Patent
Sakata et al.

(10) Patent No.: US 8,016,773 B2
(45) Date of Patent: Sep. 13, 2011

(54) LANCING APPARATUS

(75) Inventors: Tetsuya Sakata, Kyoto (JP); Daisuke Matsumoto, Kyoto (JP); Tokuo Kasai, Kyoto (JP)

(73) Assignee: Arkray, Inc. (JP)

( * ) Notice: Subject to any disclaimer, the term of this patent is extended or adjusted under 35 U.S.C. 154(b) by 137 days.

(21) Appl. No.: 10/483,909

(22) PCT Filed: Jul. 18, 2002

(86) PCT No.: PCT/JP02/07333
§ 371 (c)(1),
(2), (4) Date: Jan. 15, 2004

(87) PCT Pub. No.: WO03/007819
PCT Pub. Date: Jan. 30, 2003

(65) Prior Publication Data
US 2004/0215224 A1    Oct. 28, 2004

(30) Foreign Application Priority Data

Jul. 19, 2001 (JP) ................................. 2001-220259
Aug. 3, 2001 (JP) ................................. 2001-236976

(51) Int. Cl.
*A61B 5/00* (2006.01)
*A61B 17/14* (2006.01)
*A61B 17/32* (2006.01)
*B65D 81/00* (2006.01)

(52) U.S. Cl. .................... 600/583; 606/181; 600/584

(58) Field of Classification Search .............. 600/583, 600/584; 606/181–183
See application file for complete search history.

(56) References Cited

U.S. PATENT DOCUMENTS

| 5,108,889 | A | * | 4/1992 | Smith et al. ..................... 435/4 |
| 6,027,459 | A | * | 2/2000 | Shain et al. .................... 600/573 |
| 6,048,352 | A | * | 4/2000 | Douglas et al. ............... 606/181 |
| 6,099,484 | A |   | 8/2000 | Douglas et al. |
| 6,155,992 | A | * | 12/2000 | Henning et al. .............. 600/583 |
| 6,206,841 | B1 | * | 3/2001 | Cunningham et al. ........ 600/584 |
| 6,219,574 | B1 | * | 4/2001 | Cormier et al. ................. 604/20 |
| 6,315,738 | B1 | * | 11/2001 | Nishikawa et al. ........... 600/583 |
| 6,332,871 | B1 | * | 12/2001 | Douglas et al. ............... 600/583 |
| 6,349,229 | B1 | * | 2/2002 | Watanabe et al. ............ 600/345 |
| 6,612,111 | B1 | * | 9/2003 | Hodges et al. .................. 60/583 |
| 6,706,159 | B2 | * | 3/2004 | Moerman et al. ........ 204/403.03 |
| 6,849,052 | B2 | * | 2/2005 | Uchigaki et al. .............. 600/584 |
| 6,988,996 | B2 | * | 1/2006 | Roe et al. ...................... 600/584 |

FOREIGN PATENT DOCUMENTS

| EP | 0 988 828 | 3/2000 |
| JP | 11-347018 | 12/1999 |
| JP | 2000-231 | 1/2000 |
| JP | 2000-116626 | 4/2000 |
| JP | 2002-217804 | 8/2000 |
| JP | 2002-85384 | 3/2002 |
| WO | WO 00/40150 | 7/2000 |

* cited by examiner

*Primary Examiner* — Jeffrey G Hoekstra
(74) *Attorney, Agent, or Firm* — Studebaker & Brackett PC; Donald R. Studebaker

(57) ABSTRACT

The present invention provides a lancing apparatus (A) which includes a lancet (3) which is movable to advance in a first direction from a deeper portion in a housing (2) toward a front end of a cylindrical member (8) and an analysis component (4) disposed in the cylindrical member (8). The analysis component (4) is movable in a second direction opposite to the first direction upon receiving a force in the second direction. When skin (S) bulges, the analysis component (4) moves in the second direction following the bulging of the skin, whereby blood (b) bleeding from the skin (S) is properly introduced to the analysis component (4).

21 Claims, 19 Drawing Sheets

LANCING APPARATUS

TECHNICAL FIELD

The present invention relates to a lancing apparatus used to extract a sample such as blood through the skin of a human body for analyzing the sample.

BACKGROUND ART

For treating a diabetic, blood of the diabetic is extracted for measuring the glucose concentration in the blood, and the treatment, for example, is determined based on the measurement. An example of prior art lancing apparatus used for extracting blood is disclosed in JP-A-2000-231.

The disclosed lancing apparatus comprises a housing including a cylindrical member having an open front end, a lancet disposed in the housing, and an analysis component disposed in the cylindrical member. In using the lancing apparatus, while the front end of the cylindrical member is held pressed against skin of a human body, the lancet is advanced toward the front end of the cylindrical member. As a result, the tip end of the lancet sticks into the skin to cause bleeding from the skin. The analysis component is provided with a reagent. When the blood is supplied to the analysis component and then guided to the reagent, an intended reaction occurs between the glucose in the blood and the reagent. The glucose concentration in the blood can be determined based on the degree of the reaction. Therefore, the above lancing apparatus is convenient as compared with a lancing apparatus which is not provided with such an analysis component and which has the lancing function only.

In using the lancing apparatus with an analysis component, it is desirable to locate the analysis component as close as possible to the bleeding portion of the skin so that the blood can be reliably supplied to the analysis component. However, with the prior art device, the supply of blood is sometimes difficult for the following reasons.

When the front end of the cylindrical member of the lancing apparatus is pressed against the skin, the skin may bulge. The amount of such bulging varies depending on the softness of the skin and the strength of the force in pressing the cylindrical member. However, in the prior art lancing apparatus, the analysis component is fixed at a certain position in the cylindrical member. Therefore, depending on whether or not the skin bulges or how much the skin bulges, the distance between the bleeding portion of the skin and the analysis component may increase, which makes it difficult to properly supply the blood to the analysis component.

In extracting blood using such a lancing apparatus, it is preferable to generate negative pressure in the cylindrical member using a negative pressure pump. In such a case, the negative pressure promotes bleeding from the lanced portion of the skin so that the amount of lancing by the lancet into the skin can be advantageously reduced. However, when negative pressure is generated in this way, the skin bulges greatly due to the action of negative pressure. Therefore, the distance between the bleeding portion of the skin and the analysis component may further increase, which further makes it difficult to properly supply the blood to the analysis component.

DISCLOSURE OF THE INVENTION

An object of the present invention is to provide a lancing apparatus capable of eliminating or lessening the above-described problems.

According to a first aspect of the present invention, there is provided a lancing apparatus comprising:

a housing integrally or separately formed with a cylindrical member having an open front end, a lancet disposed in the housing and movable to advance in a first direction from a deeper portion in the housing toward the front end of the cylindrical member, and an analysis component disposed in the cylindrical member;

wherein the analysis component is movable in a second direction opposite to the first direction upon receiving a force in the second direction.

Preferably, the lancing apparatus may further comprise a negative pressure generator for generating negative pressure in the cylindrical member.

Preferably, the cylindrical member may be formed separately from the housing and mounted to the housing to partially project from the housing.

Preferably, the lancing apparatus may further comprise a holder for holding the analysis component. The holder may be supported by the cylindrical member via a resilient member capable of expanding and contracting in the first direction and the second direction.

Preferably, the holder is arranged to engage the lancet advancing in the first direction to inhibit further advancement of the lancet.

Preferably, the analysis component may include a surface oriented in the first direction for contacting skin, and the skin contacting surface may be inclined to extend toward a deeper portion in the housing as it extends closer to a central axis of the cylindrical member.

Preferably, the inclination angle of the analysis component is variable. Preferably, the lancing apparatus may further comprise a stopper for preventing the analysis component from inclining more than a predetermined angle.

Preferably, the skin contacting surface is adherent.

Preferably, the analysis component comprises a substrate, a reagent disposed on the substrate, a sample introducing portion formed at an edge of the substrate, and a capillary for guiding sample liquid adhering to the sample introducing portion to the reagent layer.

Preferably, the sample introducing portion may be defined by a surface which is made hydrophilic.

According to a second aspect of the present invention, there is provided a lancing apparatus comprising:

a housing integrally or separately formed with a cylindrical member having an open front end, a lancet disposed in the housing and movable to advance in a first direction from a deeper portion in the housing toward the front end of the cylindrical member, an analysis component disposed in the cylindrical member;

a determiner for determining whether or not a sample is introduced to the analysis component, and a negative pressure generator for generating negative pressure in the cylindrical member, wherein the lancing apparatus further comprises a controller for performing control to relieve the negative pressure generated in the cylindrical member when the determiner determines that the sample is not introduced to the analysis component within a predetermined time after the lancing apparatus is advanced toward the front end of the cylindrical member.

Preferably, the analysis component may be movable in a second direction opposite to the first direction upon receiving a force in the second direction.

Preferably, the lancing apparatus may further comprise a relief valve for causing an inside of the cylindrical member to communicate with an outside of the housing, wherein the controller is capable of opening the relief valve to relieve the negative pressure in the cylindrical member.

Preferably, the controller may control the negative pressure generator to regenerate negative pressure in the cylindrical member after negative pressure generated in the cylindrical member is relieved.

Preferably, the advancing movement of the lancet may be performed repetitively under control of the controller, and the lancet may advance again under control of the controller when the determiner determines that the sample is not introduced to the analysis component within a predetermined time after negative pressure is previously regenerated in the cylindrical member.

Preferably, the controller controls the negative pressure generator to further lower a pressure in the cylindrical member after the lancet is advanced and before the negative pressure generated in the cylindrical member is relieved.

Preferably, the lancing apparatus may further comprise an analyzer for analyzing the sample introduced to the analysis component and a notifier for notifying analysis results provided by the analyzer.

Preferably, the controller may cause the notifier to give a notice when the analysis of the sample by the analyzer is not performed within a predetermined time after the lancet is advanced.

Preferably, the lancing apparatus may further comprise a detector for detecting a pressing force applied to the cylindrical member in a direction opposite to the advancing direction of the lancet, wherein the notifier gives a notice when the pressing force detected by the detector exceeds a predetermined value.

Other features and advantages of the present invention will become clearer from the detailed description given below with reference to the accompanying drawings.

BEST MODE FOR CARRYING OUT THE INVENTION

Preferred embodiments of the present invention will be described below in detail with reference to the accompanying drawings.

Figure 1:
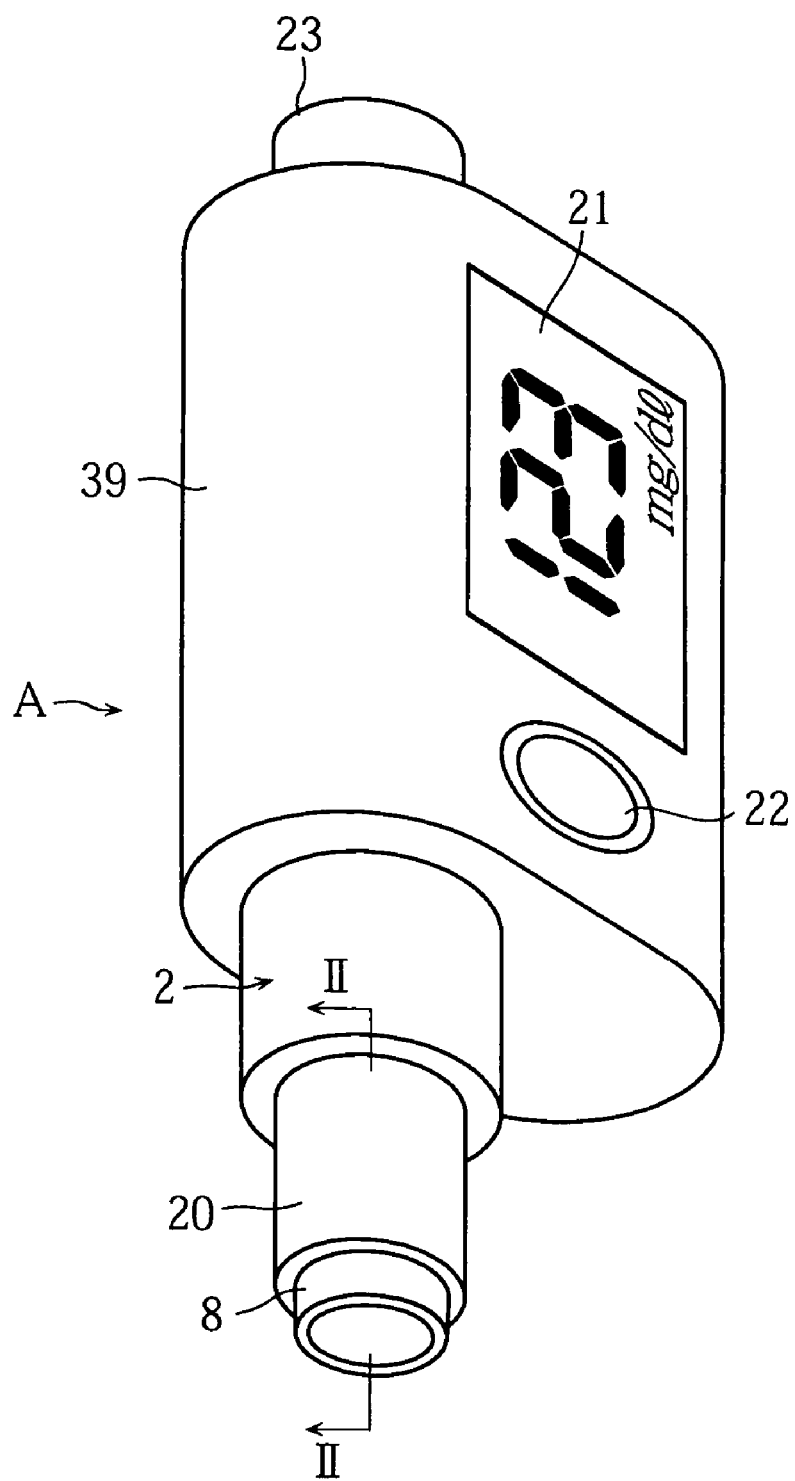
FIG. 1 is a perspective view illustrating the appearance of an example of lancing apparatus according to the present invention.

FIGS. 1 through 7 illustrate an embodiment of the present invention. As shown in FIG. 1, the lancing apparatus A in this embodiment includes a housing 2, a case 39 partially covering the housing 2, a display 21 for displaying an image, and operation switches 22 and 23. The display 21 may comprise a liquid crystal display or an LED display, for example. The case 39 incorporates a controller 9, which will be described later.

The housing 2 has a lower front end formed with a cylindrical member 20. Into the cylindrical member 20 is fitted a cylindrical member 8 formed separately from the housing 2. In using the lancing apparatus A of this embodiment, the front end 8a of the cylindrical member 8 is pressed against the skin to be lanced.

Figure 2:
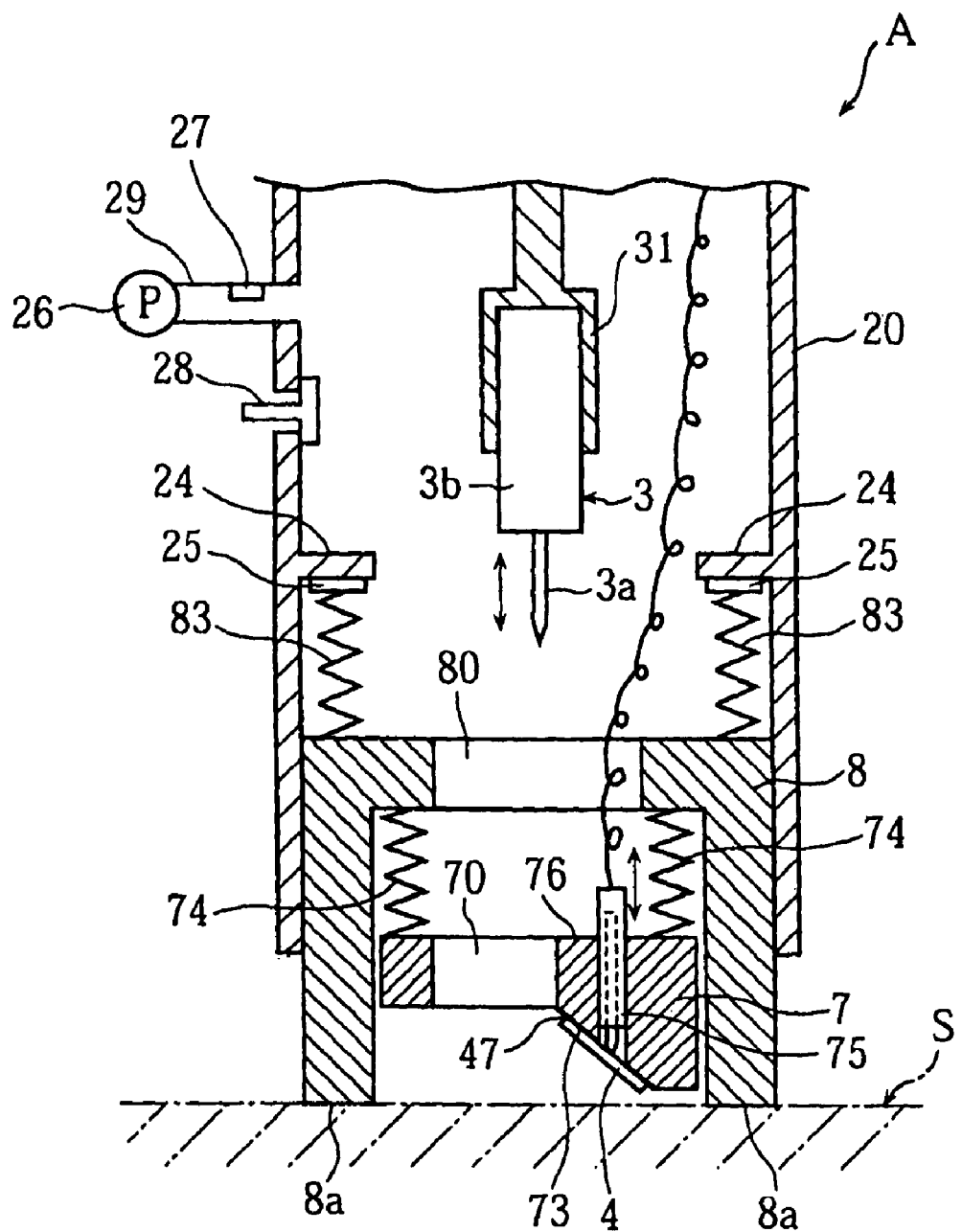
FIG. 2 is a sectional view taken along lines II-II in FIG. 1.

As clearly shown in FIG. 2, the cylindrical member 8 is supported by a flange 24 formed on an inner wall of the housing 2 via a spring 83 and is axially slidable relative to the cylindrical member 20 by expanding and contracting the spring 83. In the normal state in which the front end of the cylindrical member 8 is not pressed against the skin, part of the cylindrical member 8 closer to the front end 8a is left projecting downward from the cylindrical member 20 of the housing 2. The flange 24 is provided with a pressure sensor 25 for measuring the magnitude of the resilient force of the spring 83, and the measurement data is inputted into the controller 9.

The lancing apparatus A further includes a lancet 3, an analysis sensor 4 as an analysis component, a holder 7 for holding the analysis sensor 4, a pump 26 and a relief valve 28.

The lancet 3 and the analysis sensor 4 when used are mounted at predetermined positions in the lancing apparatus A and detached after use for replacement with new ones. In the present invention, such replacement parts are also components of the lancing apparatus.

The lancet 3 includes a main body 3b formed of synthetic resin, and a needle 3a formed of metal and projecting from the lower surface of the main body. The lancet 3 is detachably mounted to a lancet holder 31 provided in the housing 2. The lancet holder 31 is reciprocally movable axially of the cylindrical member 8 (in the vertical direction in FIG. 2) by the driving of a lancet driving mechanism 93, which will be described later. Thus, the lancet holder can move downward to advance from a deeper portion (upper portion in FIG. 2) in the housing 2 toward the front end opening of the cylindrical member 8 and can retreat for restoration to the deeper portion.

The cylindrical member 8 has an upper portion formed with an opening 80 for allowing the lancet 3 to pass therethrough.

The pump 26, which is an electrically driven pump, is connected to the housing 2 via a connection pipe 29. The pump 26 can evacuate air from the inside of the housing 2 to the outside to generate negative pressure in the cylindrical member 20 of the housing 2 and in the cylindrical member 8. The pump 26 is controlled by the controller 9, as will be described later. The pump 26 may be attached to the outer portion of the housing 2 or may be arranged in the case 39. The connection pipe 29 incorporates a pressure sensor 27, and the pressure data measured by the pressure sensor 27 is inputted into the controller 9.

The relief valve 28, which may be a solenoid valve for example, may be opened for providing communication between the inside and the outside of the housing 2 and closed for interrupting the communication. When the relief valve is opened with negative pressure generated in the housing 2, the interior of the housing 2 is returned to the atmospheric pressure.

As shown in FIGS. 4 through 7, the analysis sensor 4, which is in the form of a generally semicircular chip, comprises a substrate 40, a pair of spacers 41, a cover plate 42 and an adhesive sheet, which are laminated. On the substrate 40 is provided a reagent 44 containing enzyme which effects certain reaction (e.g. oxidation reaction) with glucose in blood, and a pair of electrodes 45 for electrically detecting the degree of the reaction. The paired spacers 41 and the cover plate 42 define a capillary 46 which serves as a passage of blood on the substrate 40. Specifically, the spacers 41 are aligned on the substrate 40 while defining a space therebetween, and a cover plate 42 is placed thereon to cover the space from above, whereby the capillary 46 is defined.

Each of the substrate 40, the adhesive sheet 43 and the paired spacers 41 is partially cut away to define a sample introducing portion 47 as a recess. When blood adheres to the sample introducing portion 47, the blood travels through the capillary 46 by capillary action to be guided to the portion of the reagent 44 sandwiched between the paired electrodes 45. As clearly shown in FIG. 6, a lower surface portion of the cover plate 42 defining the sample introducing portion 47 is hydrophilically treated by applying or attaching a hygroscopic material 49. As the hygroscopic material 49, use may be made of Vinylon. The hydrophilic treatment is advantageous for smoothly guiding the blood adhered to the sample introducing portion 47 to the capillary. The hygroscopic material 49 may be applied to portions other than the above-described portion.

The spacers 41 are respectively formed with holes 41a, whereas the cover plate 42 is formed with a pair of holes 42a communicating with the holes 41a. As will be described later, the holes 41a and 42a are used for passing a pair of measurement probes 75 for coming into contact with the paired electrodes 45. When the reagent 44 contacts blood, e.g. glucose in the blood is oxidized by oxidation reaction, whereas electron carriers in the reagent 44 are reduced by electrons from the reaction. The proportion of the electron carriers reduced corresponds to the proportion of glucose contained in blood, namely the glucose concentration, and the glucose concentration corresponds to the value of current flowing between the paired electrodes 45. Therefore, the glucose concentration in blood can be figured out based on the value of the current.

The adhesive sheet 43 is bonded to a reverse (lower) surface of the substrate 40. The adhesive sheet 43 may comprise a gel sheet containing water gel and acrylic resin, or preferably a silicone gel sheet, thereby providing adhesion. When the lower surface of the adhesive sheet 43 is brought into contact with the skin, a high adhesion is provided between the skin and the analysis sensor 4. The lower surface 43a of the adhesive sheet 43 is a surface for contact with the skin. Alternatively, for making the surface 43a adherent, a double-sided adhesive tape for providing adhesion may be bonded to the analysis sensor 4.

Figure 3:
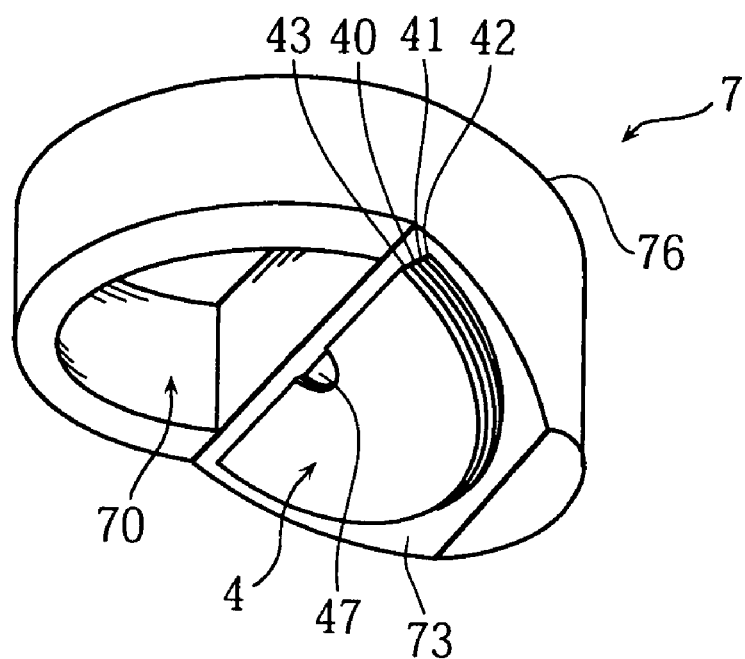
FIG. 3 is a perspective view of a sensor holder as viewed from below.
Figure 4:
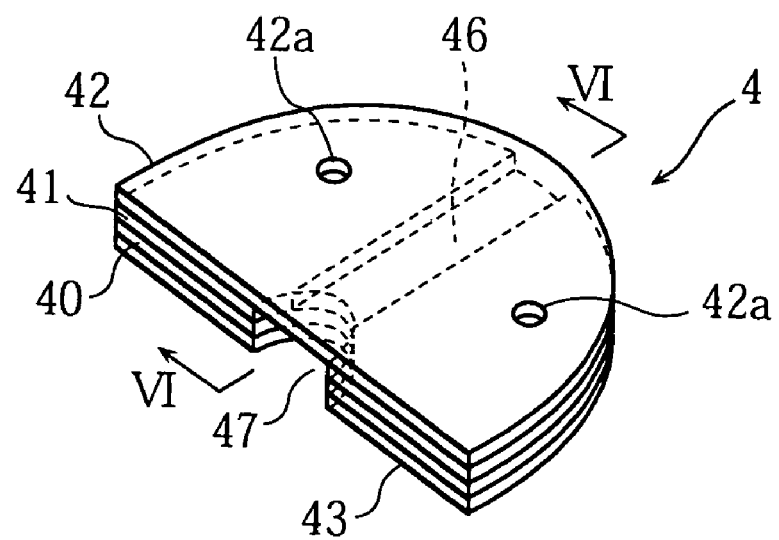
FIG. 4 is a perspective view illustrating an example of analysis sensor.
Figure 5:
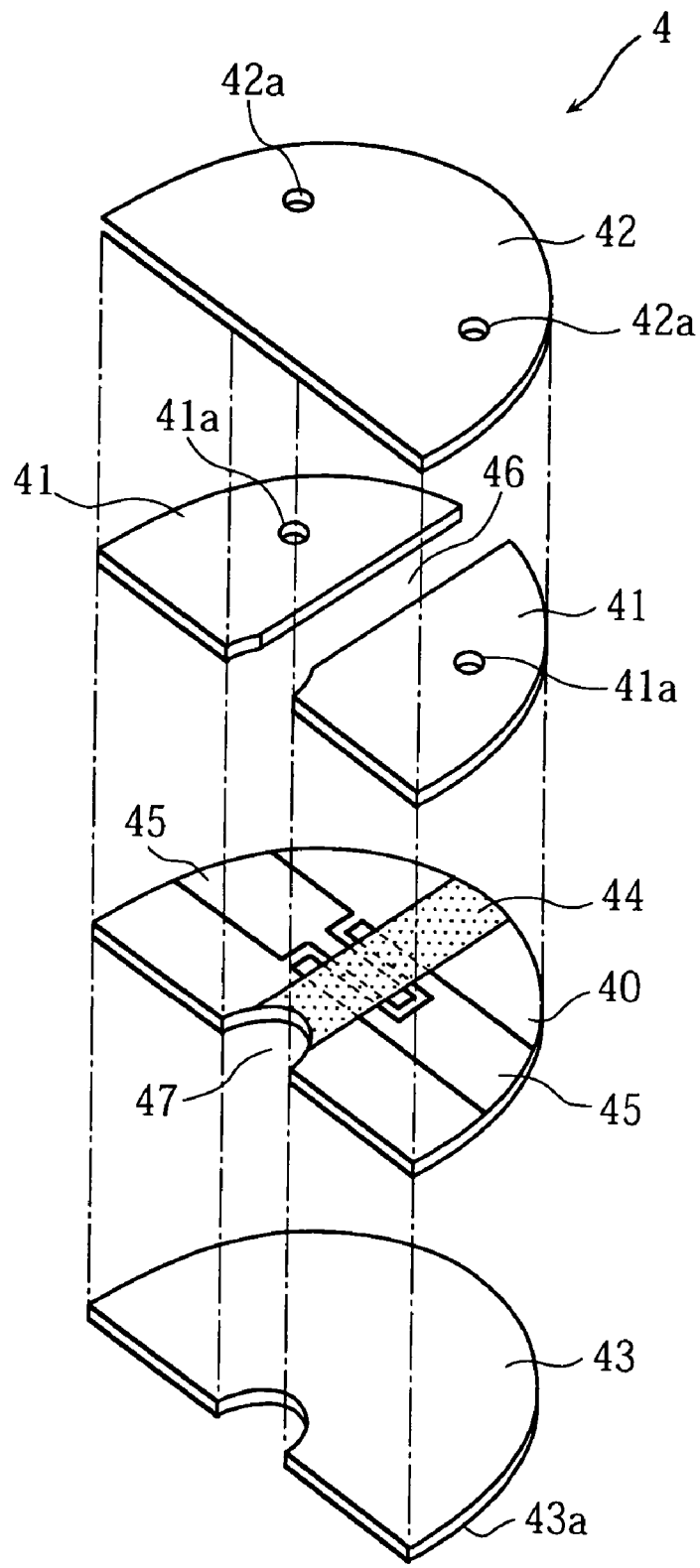
FIG. 5 is an exploded perspective view of the analysis sensor of FIG. 4.
Figure 6:
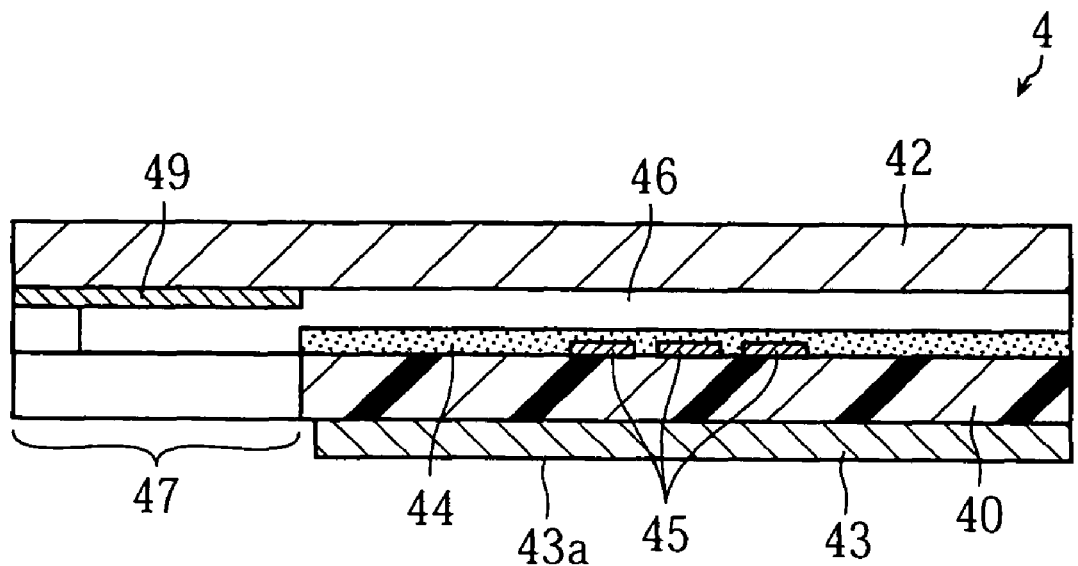
FIG. 6 is a sectional view taken along lines VI-VI in FIG. 4.
Figure 7:
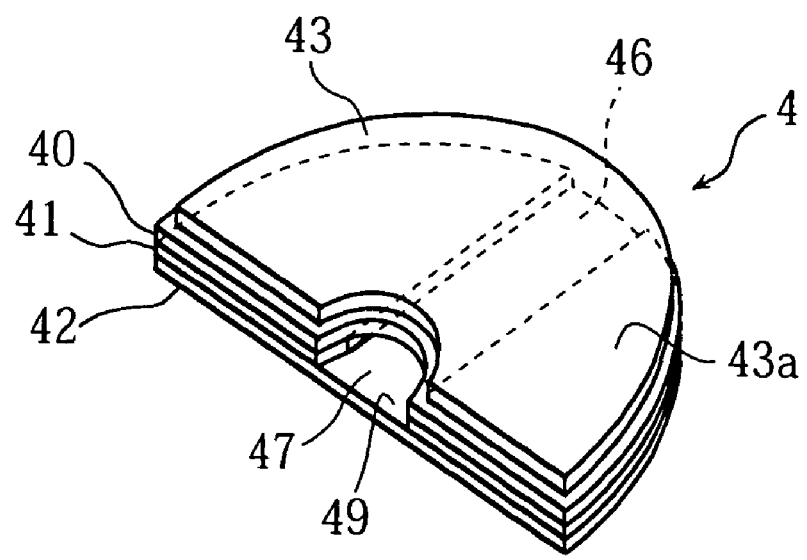
FIG. 7 is a perspective view of the analysis sensor shown in FIG. 4 as viewed from the opposite side from FIG. 4.

As clearly shown in FIG. 3, the sensor holder 7 has a mount surface 73 to which the analysis sensor 4 is mounted by bonding, for example. The mount surface 73 is inclined downwardly. As clearly shown in FIG. 2, the sensor holder 7 is suspended from the cylindrical member 8 via a spring 74. Therefore, the sensor holder 7 is reciprocally movable axially of the cylindrical member 8 by expanding and contracting the spring 74. Since the mount surface 73 is inclined, the analysis sensor 4 is also inclined. Accordingly, the surface 43a of the analysis sensor 4 for contact with the skin is inclined to be progressively closer to the central axis of the cylindrical member 8 as it extends deeper (upward in FIG. 2) into the cylindrical member 8. The analysis sensor 4 is mounted to the sensor holder 7 with the sample introducing portion 47 located close to the central axis of the cylindrical member 8.

Figure 15:
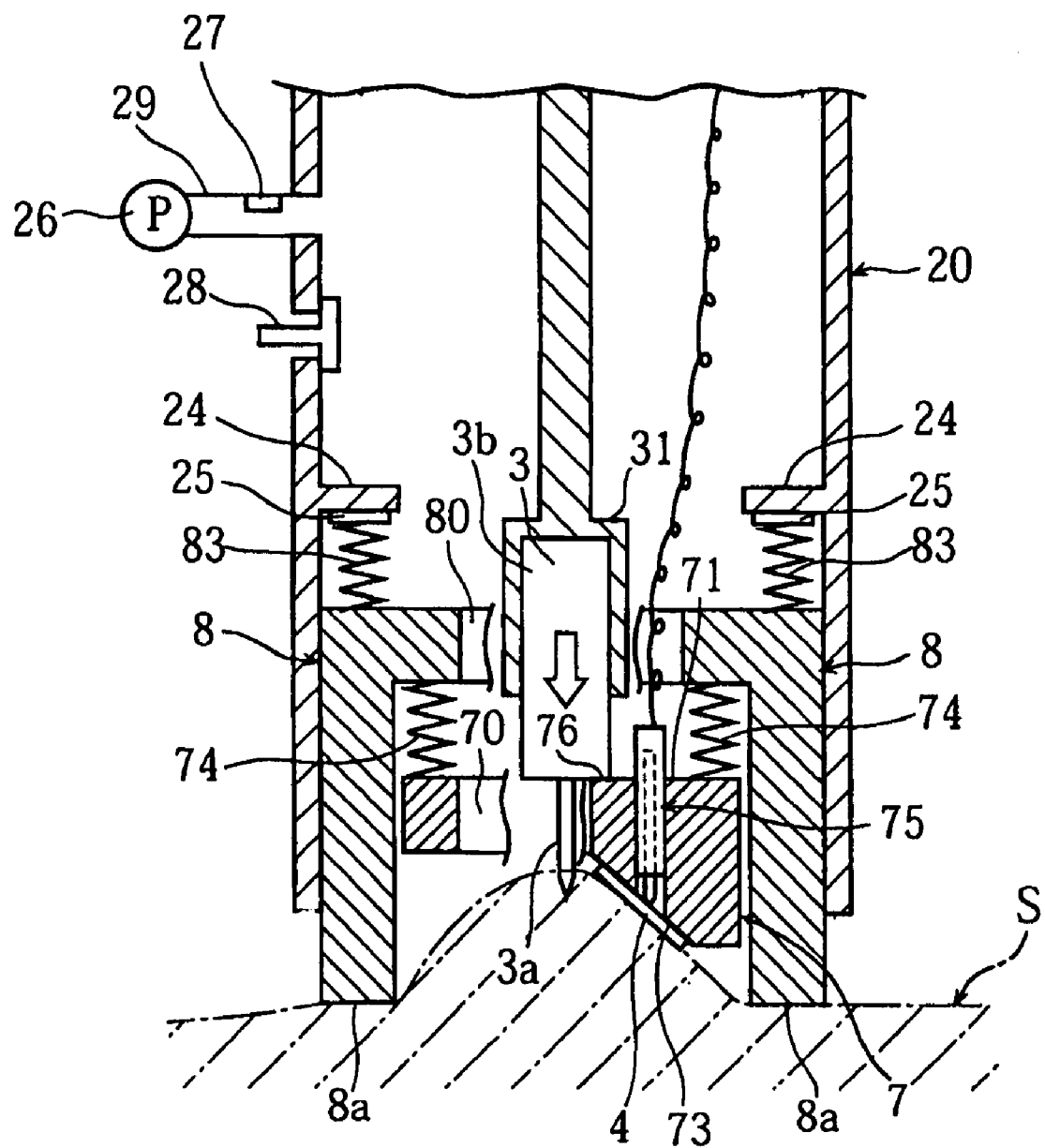
FIG. 15 is a sectional view illustrating the state in which the skin is lanced.

The sensor holder 7 is formed with a hole 70 for allowing the downwardly advancing lancet 3 to pass through. However, as shown in FIG. 15, the hole 70 does not allow the lancet 3 to pass through entirely, and the periphery of the hole 70 partially serves as a stopper 76 which engages the lower end of the main body 3b of the lancet 3 for preventing the lancet 3 from further advancing.

Figure 8:
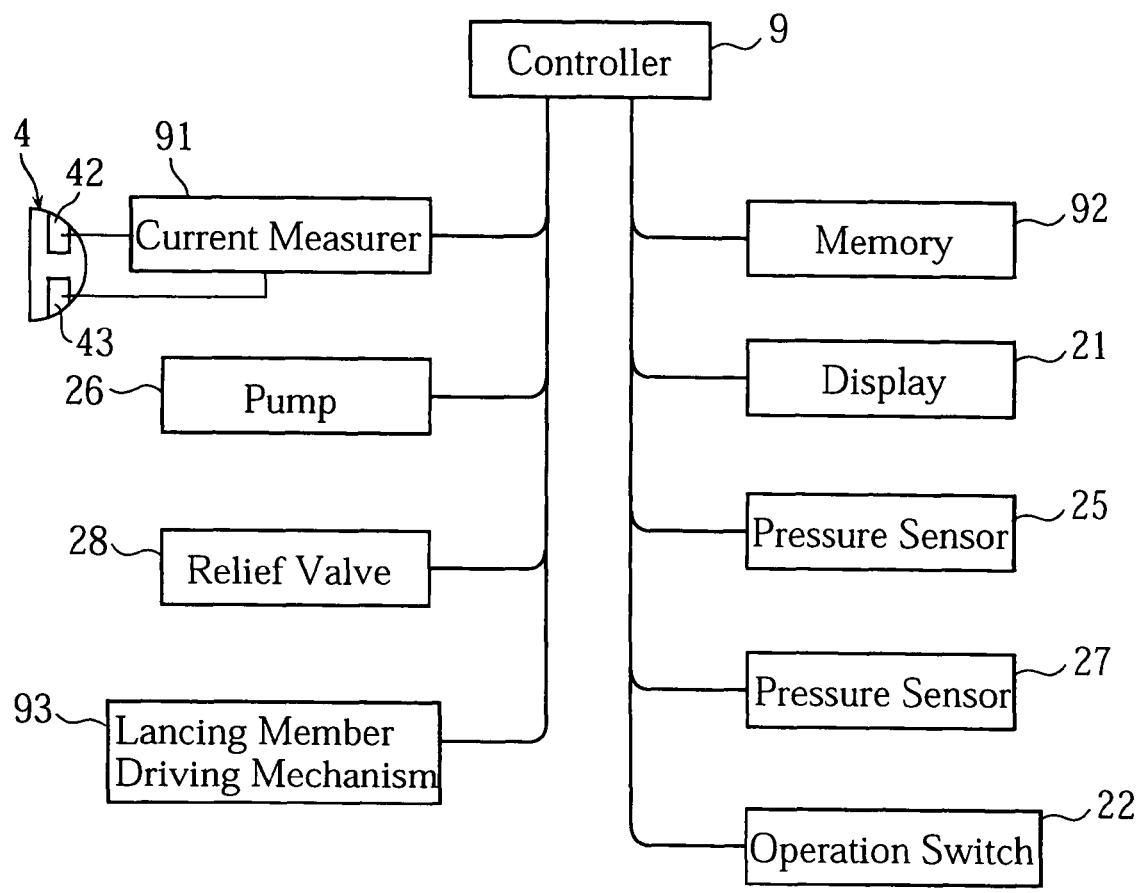
FIG. 8 is a block diagram illustrating the schematic structure of the lancing apparatus.

The paired measurement probes 75 are attached to the sensor holder 7. The measurement probes 75 are so mounted that the tip ends thereof contact the paired electrodes 45 of the analysis sensor 4. Preferably, the tip end of each probe 75 is extendable and retractable and is biased downward by the resilient force of a spring for press contact with the electrode 45 under an appropriate pressing force. As clearly shown in FIG. 8, in the lancing apparatus A of this embodiment, the controller 9 is connected to a current measurer 91, the pump 26, the relief valve 28, the lancet driving mechanism 93, a memory 92, the display 21, the pressure sensors 25 and 27, and the operation switch 22.

The current measurer 91 applies a voltage across the paired electrodes 45 of the analysis sensor 4 by utilizing the measurement probes 75 and measures the current flowing between the electrodes 45. The controller 9 calculates the glucose concentration based on the current measured by the current measurer 91.

The controller 9, which may comprise a CPU for example, performs various kinds of control based on a control program stored in the memory 92 and on electric signals from the operation switch 22 and the pressure sensors 25, 27, as will be described later. The controller 9 also has a function as a determiner for determining whether or not blood is properly supplied to the reagent 44 in the analysis sensor 4, as will also be described later. The memory 92, which may comprise a ROM or a RAM, stores data necessary for the control by the controller 9.

Next, the applications and functions of the lancet A will be described with reference to flowcharts of FIGS. 9 through 13.

First, as shown in FIG. 2, the front end 8a of the cylindrical member 8 of the lancing apparatus A is pressed against the skin S of a human body as a target of lancing (Step S1). Then, the controller 9 checks whether the front end 8a is pressed against the skin S too strongly or not (Step 2). Specifically, when the front end 8a is pressed against the skin S, the pressure sensor 25 measures the pressing force. When the measurement value exceeds a predetermined value, the controller 9 determines that the user is pressing the front end 8a too strongly against the skin S (Step S2: YES), and causes the display 21 to display a notice to that effect (Step S3). Upon seeing the display, the user can make adjustments to press the front end 8a against the skin S with a proper pressing force. In this way, it is possible to prevent excessive tension of the skin S which may cause insufficient bulging when the pressure in the cylindrical member 8 is reduced for bulging the skin S, as will be described later.

Figure 14:
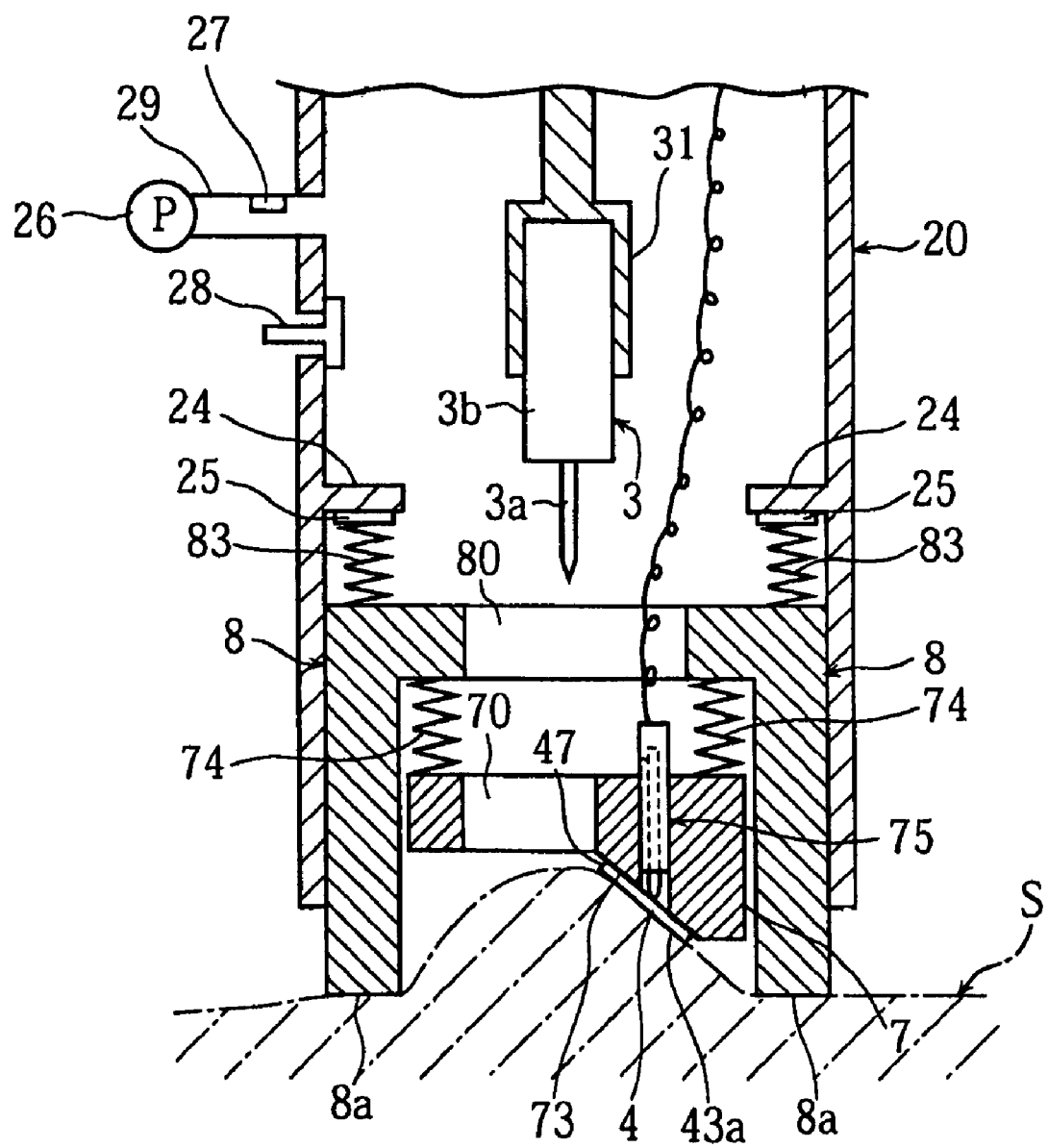
FIG. 14 is a sectional view illustrating the state in which the skin is bulged.

Subsequently, when the user presses the operation switch 22 of the case 2 (Step S4: YES), the controller 9 drives the pump 26 (Step S5). By this operation, negative pressure is generated in the cylindrical member 8. As a result, the skin S bulges as shown in FIG. 14 to come into contact with the skin contact surface 43a of the analysis sensor 4. Since the surface 43a is inclined, it closely fits to an inclined surface of the bulged portion of the skin S. Since the surface 43a is provided by the adhesive surface of the adhesive sheet 43, the adhesion of the analysis sensor to the skin S is further enhanced. Since the analysis sensor 4 closely fits to the skin S to avoid formation of a large gap between the analysis sensor 4 and the skin S, the blood is prevented from unduly flowing into such a gap.

The controller 9 monitors pressure measurements by the pressure sensor 27 and determines whether or not the measured pressure has reached a predetermined value (Step S6). If the controller 9 determines that the measured pressure has not reached the predetermined value (Step S6: NO), the controller continues the driving of the pump 26 to further lower the pressure in the cylindrical member 8. Thus, the skin S further bulges to push the analysis sensor 4 upward. As a result, the analysis sensor 4 moves upward while contracting the spring 74. The analysis sensor 4 stops at the position where the bulging force of the skin S and the resisting force of the spring 74 are in equilibrium.

In this way, since the analysis sensor 4 is lifted following the bulging of the skin S, the analysis sensor 4 does not unduly inhibit the bulging of the skin S. Further, the positional relationship between the top of the bulging portion of the skin S and the sample introducing portion 47 is kept generally constant regardless of how much the skin S bulges. This is preferable for properly guiding the blood to the sample introducing portion 47 of the analysis sensor 4, as will be described later.

If the controller 9 determines that the pressure measured by the pressure sensor 27 has reached the predetermined value (Step S6: YES), the controller 9 drives the lancet driving mechanism 93. As a result, the lancet holder 31 and the lancet 3 advance into the cylindrical member 8 and then retreat to their original position. As shown in FIG. 15, when the lancet 3 advances, the needle 3a sticks into the skin S (Step S7). During this advancing movement of the lancet 3, the main body 3b engages the stopper 76, so that the lancet 3 is prevented from advancing more than a predetermined distance. Thus, the needle 3a is prevented from sticking into the skin S more than a predetermined amount, thereby avoiding great damage to the skin S.

Alternatively, in the present invention, the advancing/retreating movement of the lancet 3 may be performed by the user's manipulation of the operation switch 23 without relying on the controller 9. In that case, when the pressure measured by the pressure sensor 27 has reached the predetermined value (Step S6: YES), the controller 9 instructs the display 21 to indicate that the driving of the lancet 3 is allowable. Upon seeing the display, the user presses the operation switch 23 to move the lancet 3.

Figure 18:
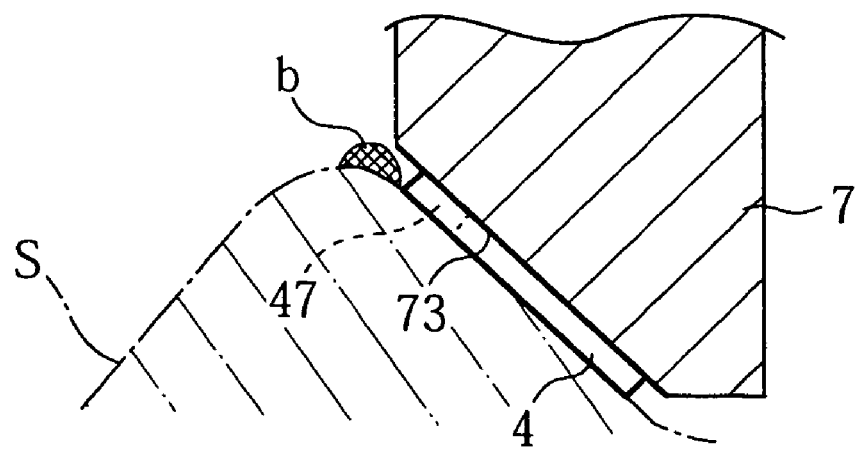
FIG. 18 illustrates positional relationship between skin and the analysis sensor.

The above lancing causes bleeding from the skin S. At this time, the negative pressure generated in the cylindrical member 8 promotes the bleeding from the skin S. As shown in FIG. 18, the blood b from the skin S tends to flow along the surface of the bulged skin S. However, since the analysis sensor 4 is in close contact with the skin S as previously noted, the blood b cannot flow between the sensor and the skin. Therefore, the blood b is properly guided to the sample introducing portion 47. Moreover, the analysis sensor 4 moves upward following the bulging of the skin S, so that the positional relationship between the top of the bulging portion of the skin S and the sample introducing portion 47 is kept generally constant. Therefore, the sample introducing portion 47 can be kept close to the bleeding portion regardless of the degree of bulging of the skin S. This also contributes to the reliable guiding of the blood b to the sample introducing portion 47. Further, the sample introducing portion 47 opens widely as compared with the capillary 46, which is also advantageous for reliable guiding of the blood b to the sample introducing portion 47.

The blood guided to the sample introducing portion 47 travels through the capillary 46 by capillary action. Since the hygroscopic material 49 provided at the sample introducing portion 47 is highly hydrophilic, the blood b is unlikely to stagnate between the sample introducing portion 47 and the skin S, whereby the travelling of the blood b to the capillary 46 is promoted. The blood b travelling in this way is readily supplied to the reagent 44.

The controller 9 determines whether or not a sufficient amount of blood needed for concentration measurement is supplied to the reagent 44 (Step S8). Specifically, upon supply of an amount of blood b to the reagent 44, the above-described redox reaction occurs, which causes current to flow between the paired electrodes 45. When the current exceeds a predetermined threshold value, the controller 9 determines that the amount of the blood supplied to the reagent 44 is sufficient (Step S8: YES). When the controller 9 determines that the amount of blood b supplied is not sufficient (Step S8: NO), the controller continues to monitor whether or not the blood b is sufficiently supplied until a predetermined time elapses (Step S12).

If the controller 9 determines that the blood b is properly supplied to the reagent 44 (Step S8: YES), the controller stops the driving of the pump 26 while opening the relief valve 28 (Step S9). As a result, the interior of the cylindrical member 8 returns to the atmospheric pressure, which makes it easy to remove the cylindrical member 8 from the skin S. Thereafter, the controller 9 calculates the glucose concentration in the blood b based on the value of the current measured by the current measurer 91 (Step S10) and instructs the display 21 to show the resulting value (Step S11).

As previously noted, in the lancing apparatus A in this embodiment, the analysis sensor 4 follows the bulging of the skin S. Therefore, the blood b can be reliably guided to the sample introducing portion 47 of the analysis sensor 4. However, the degree of bulging of the skin S varies largely depending on e.g. the softness and thickness of the skin S. Therefore, even with an equal level of negative pressure, the degree of bulging of the skin S may sometimes be extremely large or extremely small. In such a case, the blood b may not be properly guided to the sample introducing portion 47. In that case, the lancing apparatus A in this embodiment performs secondary control to readily guide the blood b to the sample introducing portion 47.

Figure 9:
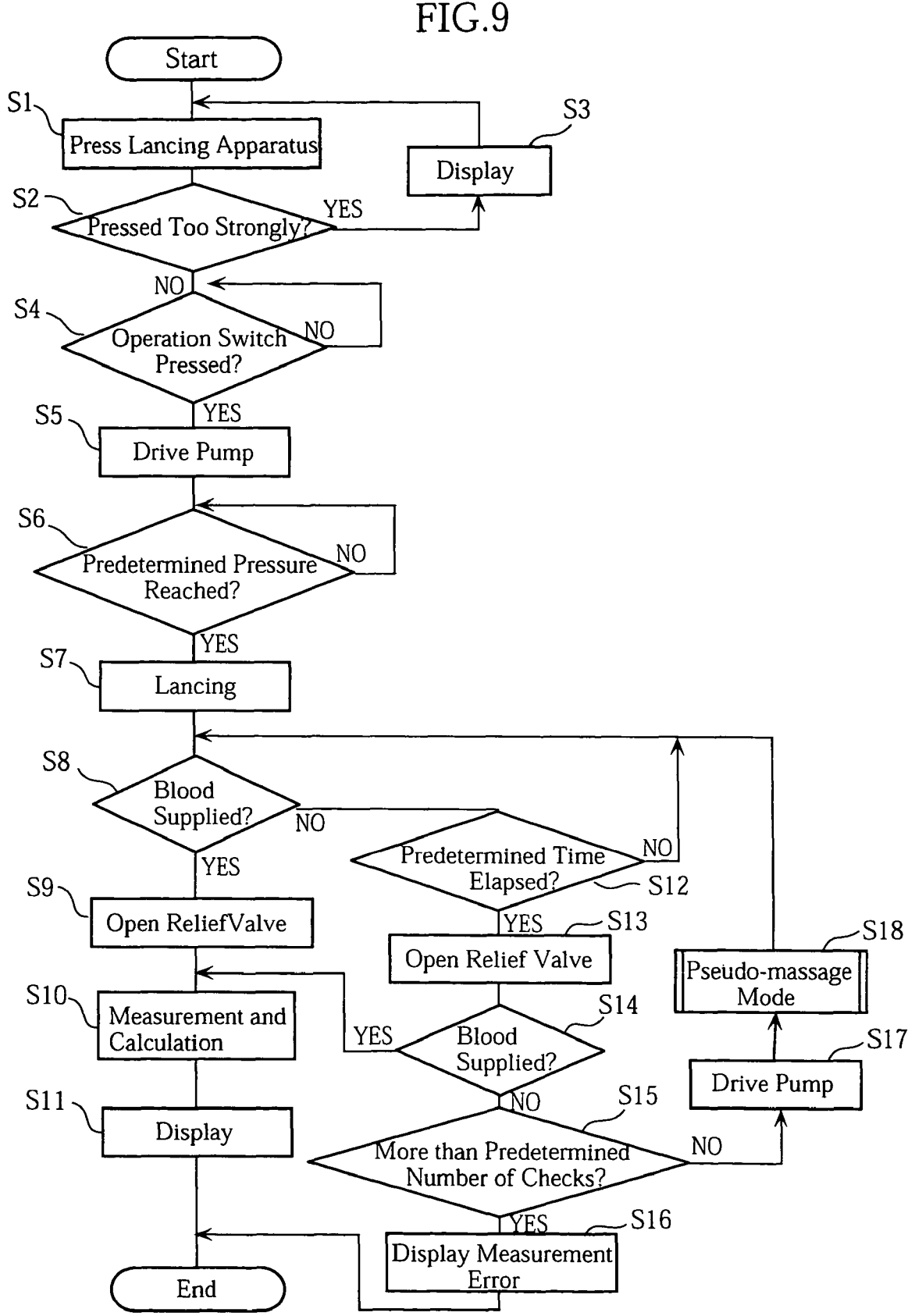
FIG. 9 is a flowchart illustrating operation control by the controller.
Figure 16:
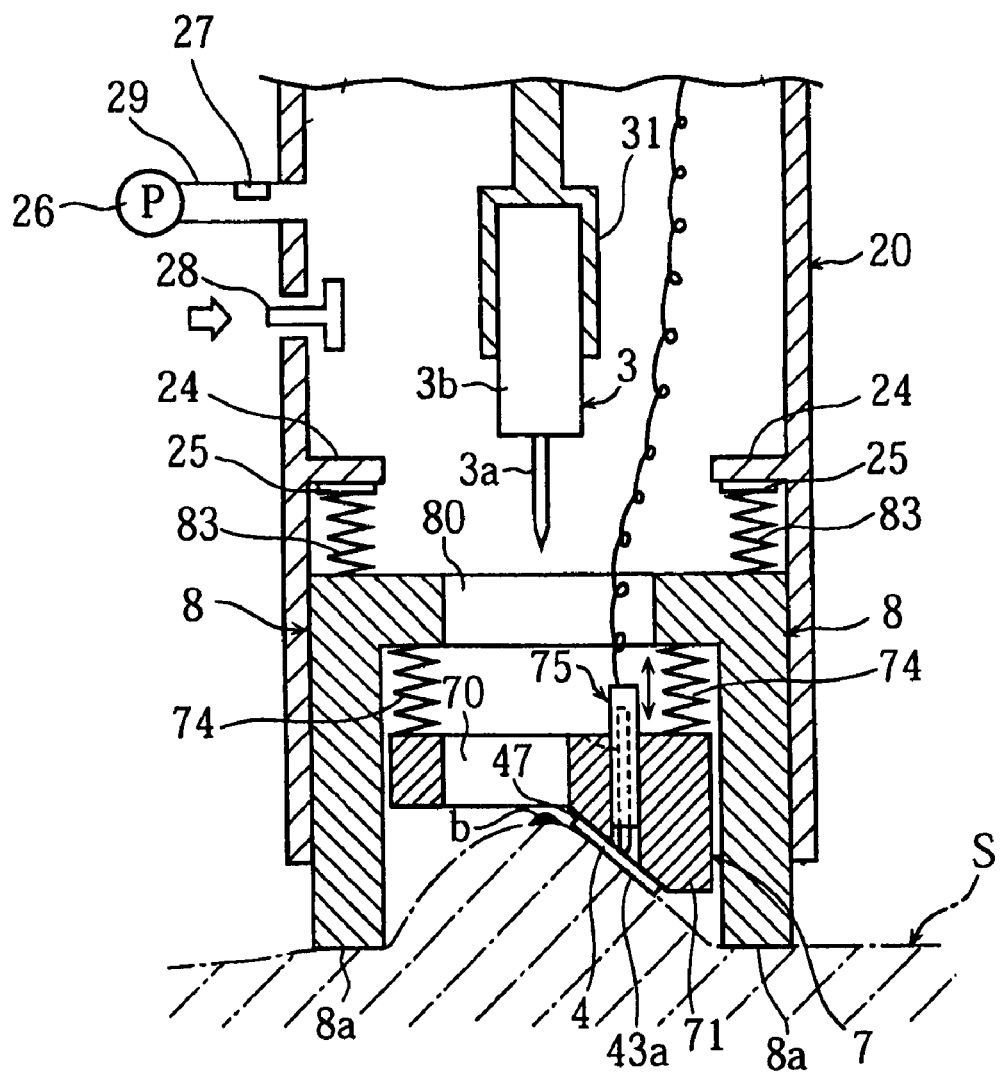
FIG. 16 is a sectional view illustrating the state after the skin is lanced.

Specifically, if the controller 9 determines that an appropriate amount of blood b is not supplied to the reagent 44 in Step S8 in FIG. 9 and a predetermined time has elapsed from the lancing without detecting proper supply of the blood b (Step S12: YES), the controller 9 stops the driving of the pump 26 while opening the relief valve 28, as shown in FIG. 16 (Step S13). As a result, the negative pressure in the cylindrical member 8 is relieved.

At this time, instead of abruptly returning the interior of the cylindrical member 8 to the atmospheric pressure, the internal pressure of the cylindrical member 8 may be gradually returned to the atmospheric pressure by adjusting the opening degree of the relief valve 28 and the driving of the pump 26 under control of the controller 9. Such a control provides the following advantages.

Figure 17:
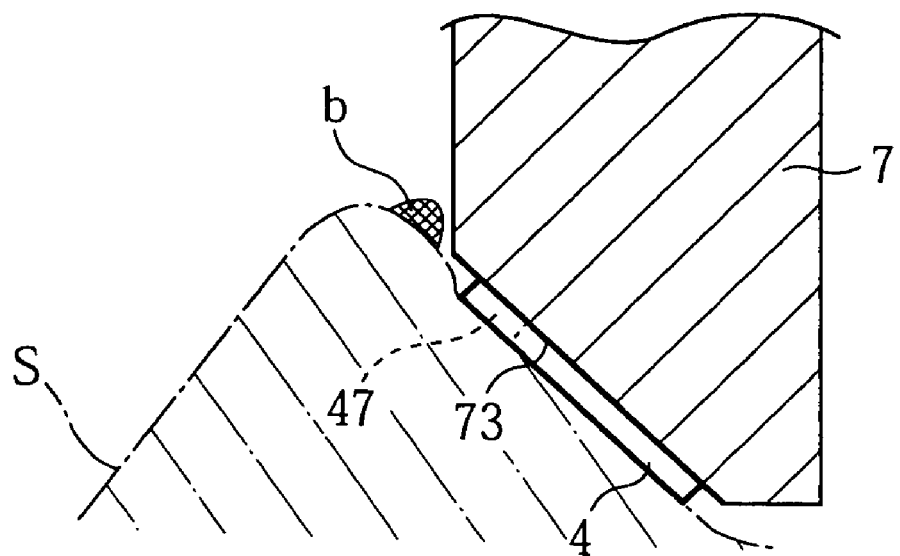
FIG. 17 illustrates positional relationship between skin and the analysis sensor.

When negative pressure is generated in the cylindrical member 8 by driving the pump 26 in Step S5 in FIG. 9, the skin S may bulge largely as shown in FIG. 17 if the skin S is considerably soft. When the skin S is bulged, the top of the bulging portion is locally swelled. In this case, when the top of the bulging portion bleeds as a result of lancing, a large distance exists between the blood b and the sample introducing portion 47 of the analysis sensor 4. Therefore, part of the sensor holder 7 may block the path from the bleeding portion to the sample introducing portion 47. In such a case, proper guiding of the blood b to the sample introducing portion 47 is difficult.

However, when the pressure in the cylindrical member 8 is gradually returned to the atmospheric pressure as noted above, the local swelling at the top of the skin S shrinks with the analysis sensor 4 closely contacting the skin S for a while. Therefore, the bleeding portion comes closer to the sample introducing portion 47, and part of the sensor holder 7 does not block the path from the bleeding portion to the sample introducing portion 47. Therefore, the blood b can be reliably guided to the sample introducing portion 47. It is preferable that the increasing of pressure in the cylindrical member 8 is performed as slowly as possible so that the bulged portion of the skin S shrinks slowly. By this, the bleeding portion and the sample introducing portion 47 can be located close to each other for a relatively long time, which contributes to reliable guiding of the blood b to the sample introducing portion 47.

After the relief valve 28 is opened as noted before, the controller 9 determines again whether or not the blood b is properly supplied to the reagent 44 (Step S14). This process step is performed similarly to Step S8. If it is determined that the blood b is properly supplied to the reagent 44 (Step S14: YES), the process proceeds to Step S10 and the following step similarly to the above.

If the blood b is not properly guided to the sample introducing portion 47 in spite of the above operation control (Step S14: NO), the controller 9 determines whether or not the controller has checked the proper guiding of the blood b to the sample introducing portion 47 more than a predetermined number of times (Step S15). If the number of checks exceeds the predetermined value (Step S15: YES), the controller 9 determines that the measurement of glucose concentration is impossible and instructs the display 21 to show a notice to that effect (Step S16).

On the other hand, if the number of checks does not exceed the predetermined value (Step S15: NO), the controller 9 drives the pump 26 (Step S17). As a result, the interior of the cylindrical member 8 undergoes a pressure drop again, whereby the skin S is bulged. The following control mode by the controller 9 is a pseudo-massage mode, which provides advantages similar to those provided by massaging the surface of the skin S with fingers (Step S18).

Figure 10:
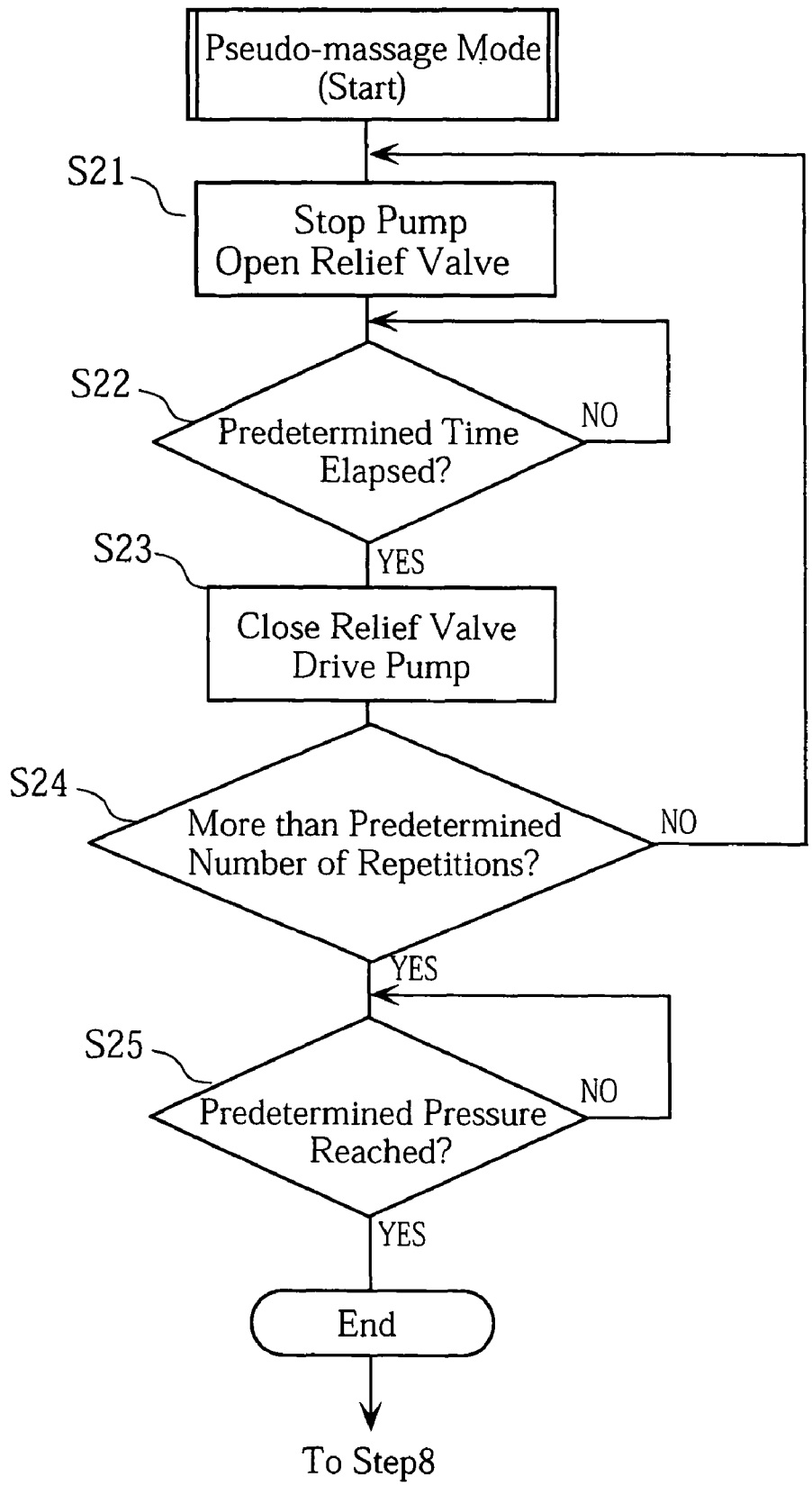
FIG. 10 is a flowchart illustrating operation control by the controller.

In the pseudo-massage mode after the driving of the pump 26 is started, the pump 26 is stopped while the relief valve 28 is opened (Step S21), as shown in FIG. 10. As a result, the negative pressure is reduced. Subsequently, after a predetermined time elapsed (Step 22: YES), the relief valve 28 is closed and the pump 26 is driven (Step 23), thereby increasing negative pressure. The above series of operations are repeated a predetermined number of times (Step S24). The pressure variation caused in this way provides the skin S with effects like those provided by massaging the skin. Therefore, the blood circulation is promoted, which promotes bleeding from the skin S. The blood circulation promoting effect does not necessarily increase in proportion to the number of repetitions of pressure variation. Further, as the number of repetitions increases, the time taken for measurement increases. Therefore, it is reasonable to provide a certain limit to the number of repetitions of the above-noted pressure variation. In reducing negative pressure in the pseudo-massage mode, it is preferable to keep the interior of the cylindrical member 8 under negative pressure of such a level that holds the analysis sensor 4 in contact with the skin S, instead of abruptly returning the interior of the cylindrical member to the atmospheric pressure. When the internal pressure of the cylindrical member 8 reaches a predetermined negative level after the pressure variation is repeated a predetermined number of times (Step S25: YES), the process by the controller 9 returns to Step S8 in FIG. 9. In this way, even when the measurement of glucose concentration in blood b seems to be impossible due to insufficient bleeding from the skin S, proper measurement of the blood glucose concentration becomes possible by performing the pseudo-massage mode.

Figure 11:
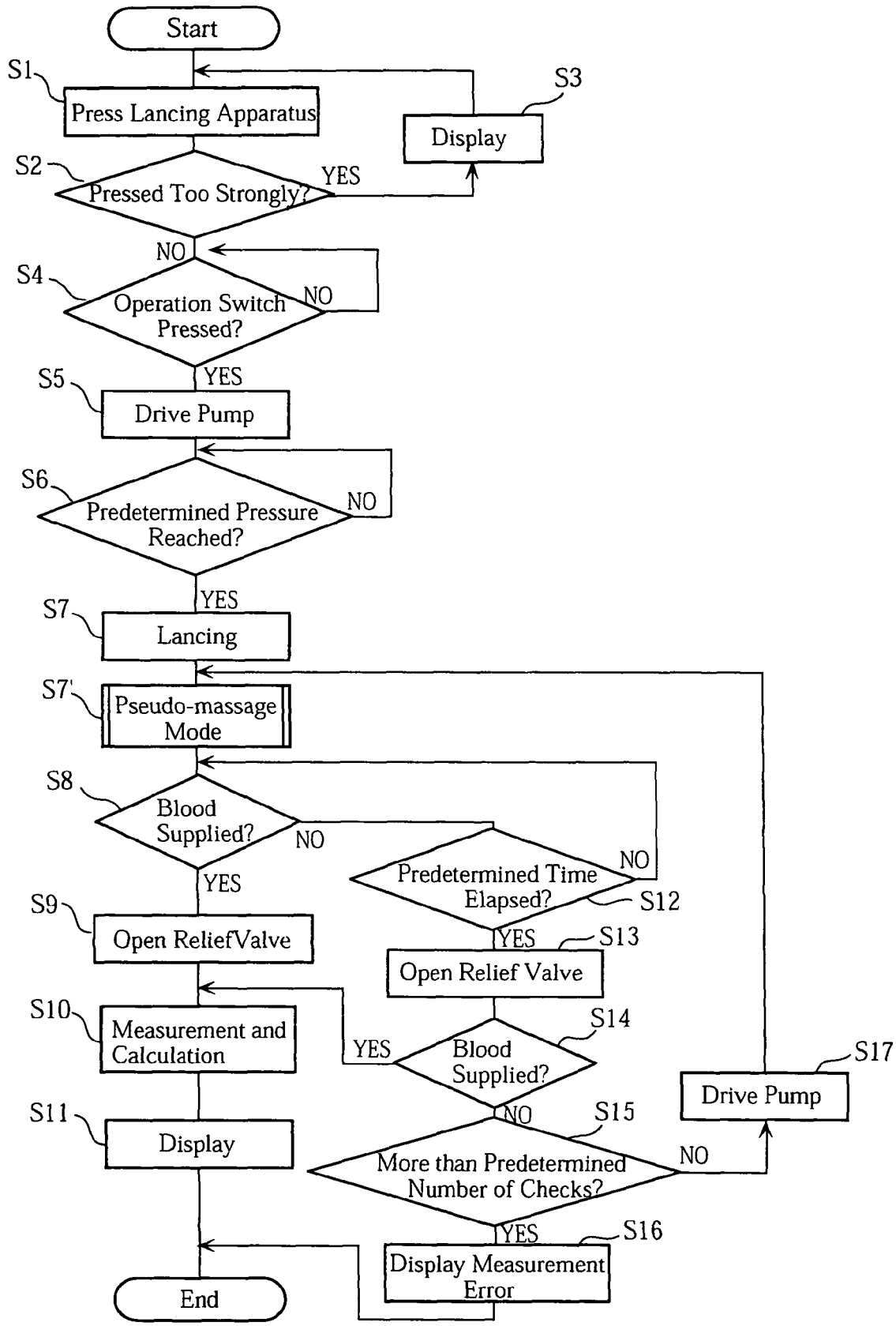
FIG. 11 is a flowchart illustrating operation control by the controller.
Figure 12:
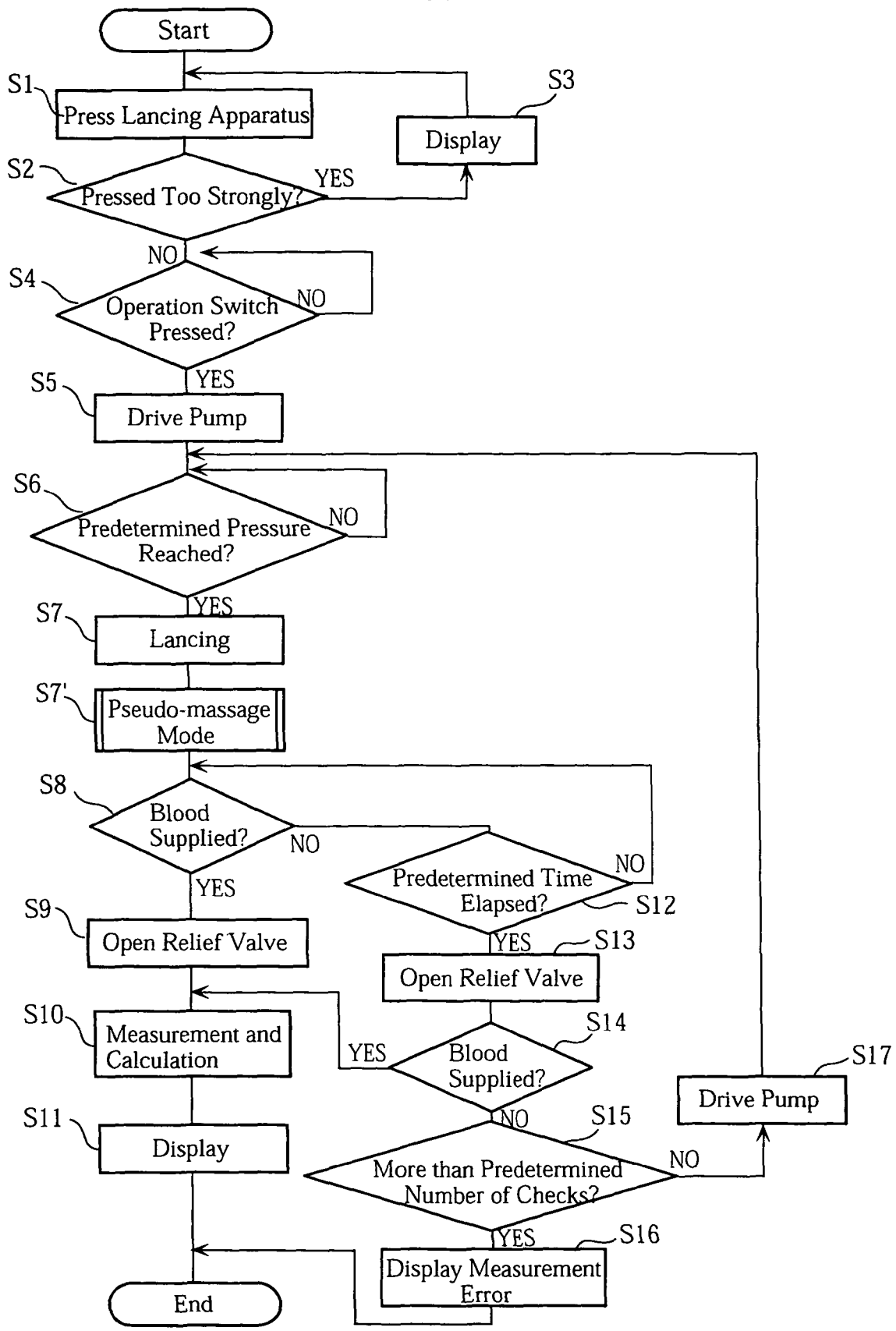
FIG. 12 is a flowchart illustrating operation control by the controller.
Figure 13:
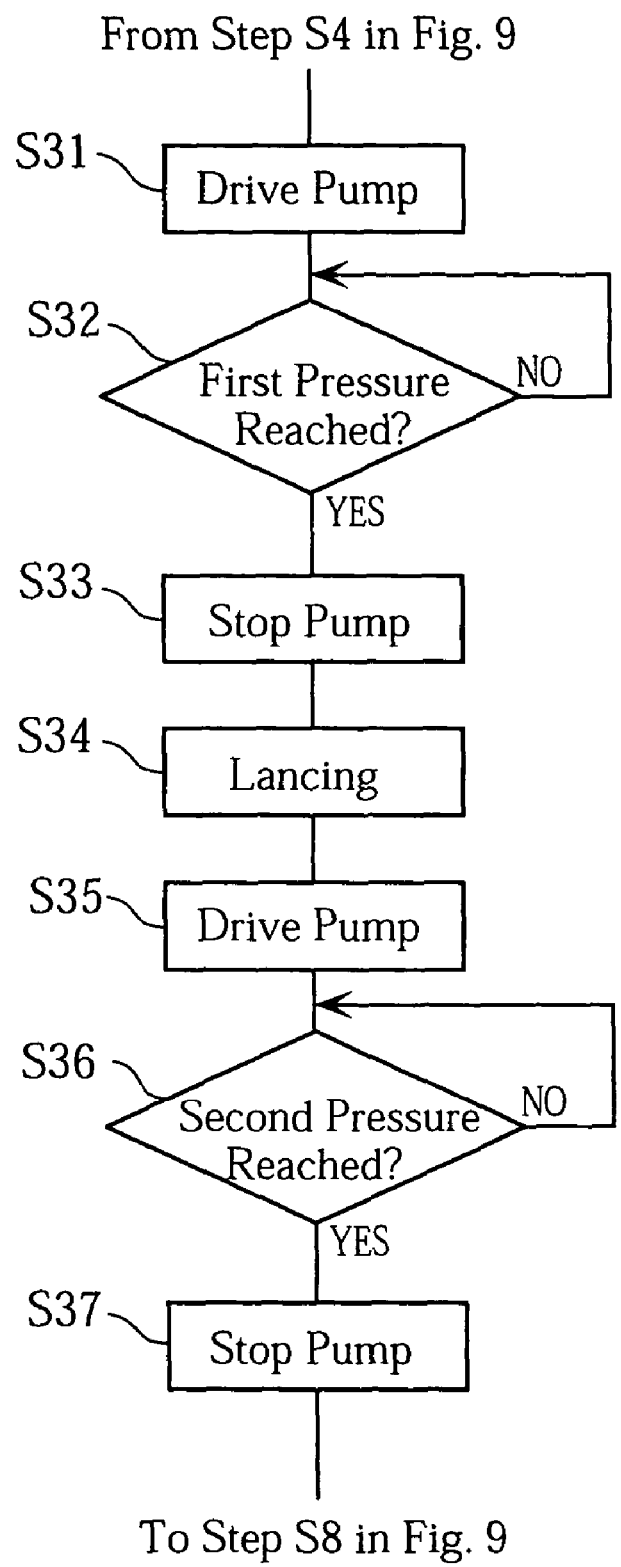
FIG. 13 is a flowchart illustrating operation control by the controller.

FIGS. 11 through 13 are flowcharts illustrating other examples of operation control of the lancing apparatus A.

In the operation control shown in the flowchart of FIG. 11, the pseudo-massage mode shown in FIG. 10 is performed as Step S7', which is performed directly after the skin S is lanced by the lancet 3 in Step S7. Thereafter, determination is made as to whether or not the blood b is properly supplied to the reagent 44 (Step S8).

In this way, when the pseudo-massage mode is performed directly after the skin S is lanced, bleeding from the skin S is further promoted. Therefore, a sufficient amount of blood b is more likely to be guided to the analysis sensor 4 than in the case of the flowchart shown in FIG. 9.

In the operation control shown in the flowchart of FIG. 12, the process returns to Steps S6 and S7 after Step S17 is performed in which the pump 26 is driven to generate a negative pressure in the cylinder body 8 again. Specifically, in this operation control, the lancing of the skin S in Step S7 is performed again after the negative pressure is generated again.

In the above operation control, even when the first lancing is not properly performed due to deviation of a lancing position, the blood b can be properly supplied to the reagent 44 of the analysis sensor 4 by performing the second lancing at the proper position.

In any of the operation controls shown in the flowcharts of FIGS. 9, 11 and 12, the relief valve 28 is opened to relieve the negative pressure in the cylindrical member 8 (Step S13) after it is determined that blood b is not supplied to the analysis sensor 4 (Step S8: NO). However, instead of relieving the negative pressure, the pseudo-massage mode shown in FIG. 10 may be performed. Further, when the blood b is not properly supplied to the reagent 44 of the analysis sensor 4 even after the pseudo-massage mode is performed, the lancing of the skin S may be performed again.

FIG. 13 shows a flowchart of operation control which may replace the process steps of the foregoing operation control subsequent to Step S4 for making determination as to the pressing of the operation switch 22 and prior to Step S8 for making determination as to whether or not blood b is properly supplied to the reagent 44.

In this operation control, depressurization is performed twice, i.e. before and after the skin S is lanced. Specifically, in this operation control, the controller 9 drives the pump 26 (Step S31) to depressurize the cylindrical member 8 and then determines whether or not the pressure measured by the pressure sensor 27 has reached a predetermined first value (Step S32). The first pressure is lower than the atmospheric pressure and higher than a second pressure to be described later.

If it is determined that the value outputted from the pressure sensor 27 has reached the first value (Step 32: YES), the controller 9 temporarily stops the driving of the pump 26 (Step S33). Thus, the interior of the cylindrical member 8 is kept at a pressure slightly lower than the atmospheric pressure, thereby causing the skin S to bulge. However, the degree of bulging in this stage is such a level that brings the skin into contact with the surface 43*a* but does not cause the analysis sensor 4 to be raised by the skin. Subsequently, the controller 9 causes the lancing operation (Step S34) and then drives the pump 26 again (Step S35). Thereafter, the controller determines whether or not the pressure measured by the pressure sensor 27 has reached the second value (Step S36). When the measured pressure has reached the second value (Step S36: YES), the driving of the pump 26 is stopped (Step S37).

By the above operation control, the skin S further bulges toward a deeper portion in the cylindrical member 8, and the bulging amount is large. As a result, bleeding from the skin S is promoted due to the growth of the cut formed at the skin S by lancing as well as due to the additional suction under the negative pressure. Therefore, in this control again, it is possible to supply a sufficient amount of blood b to the reagent 44 of the analysis sensor 4.

FIGS. 19 through 22 illustrate other structural examples of lancing apparatus according to the present invention. In these figures, the elements which are identical or similar to those of the above-described embodiment are designated by the same reference signs as those used for the foregoing embodiment.

Figure 19:
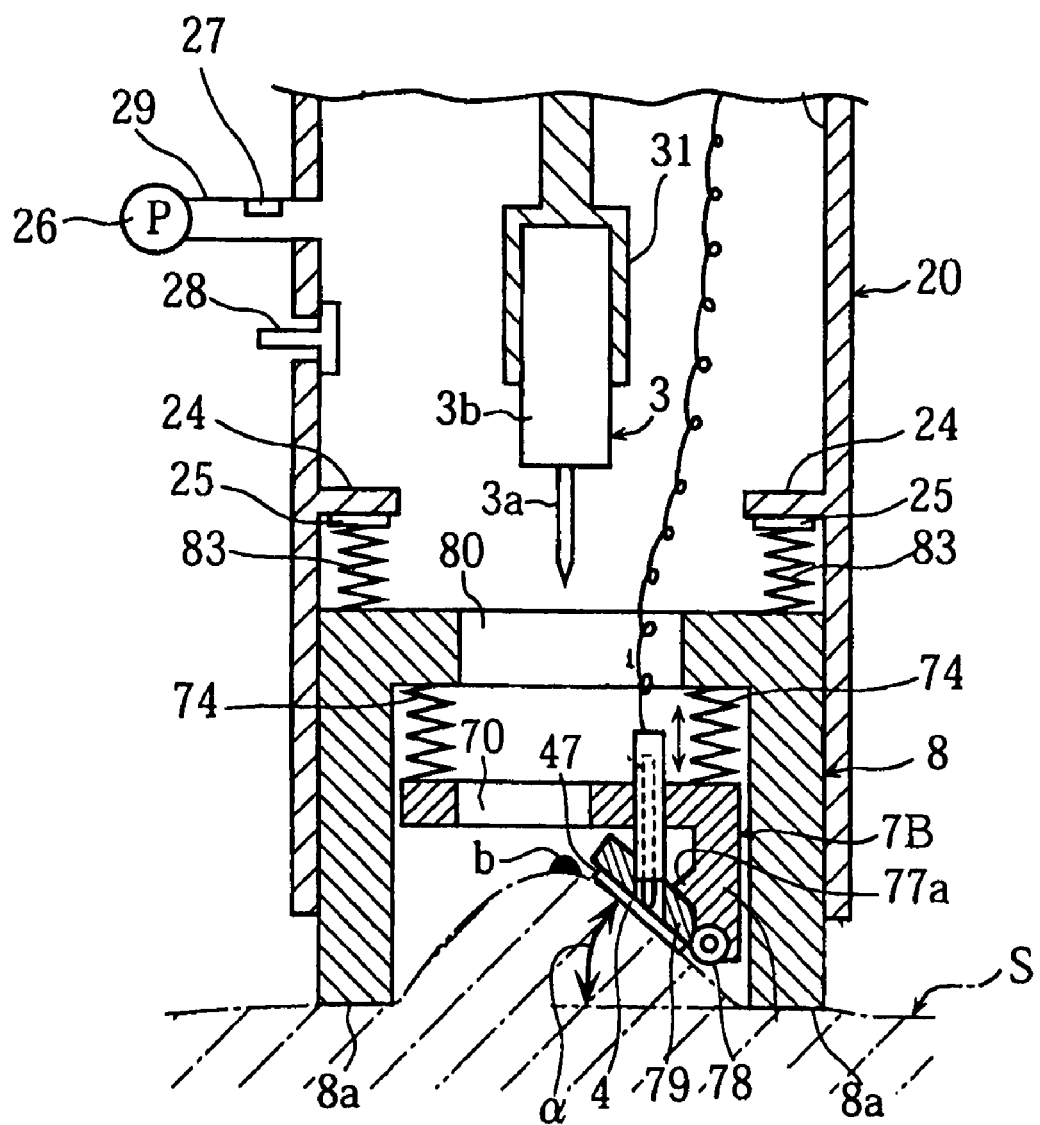
FIG. 19 is a sectional view illustrating a principal portion of another lancing apparatus according to the present invention.
Figure 20:
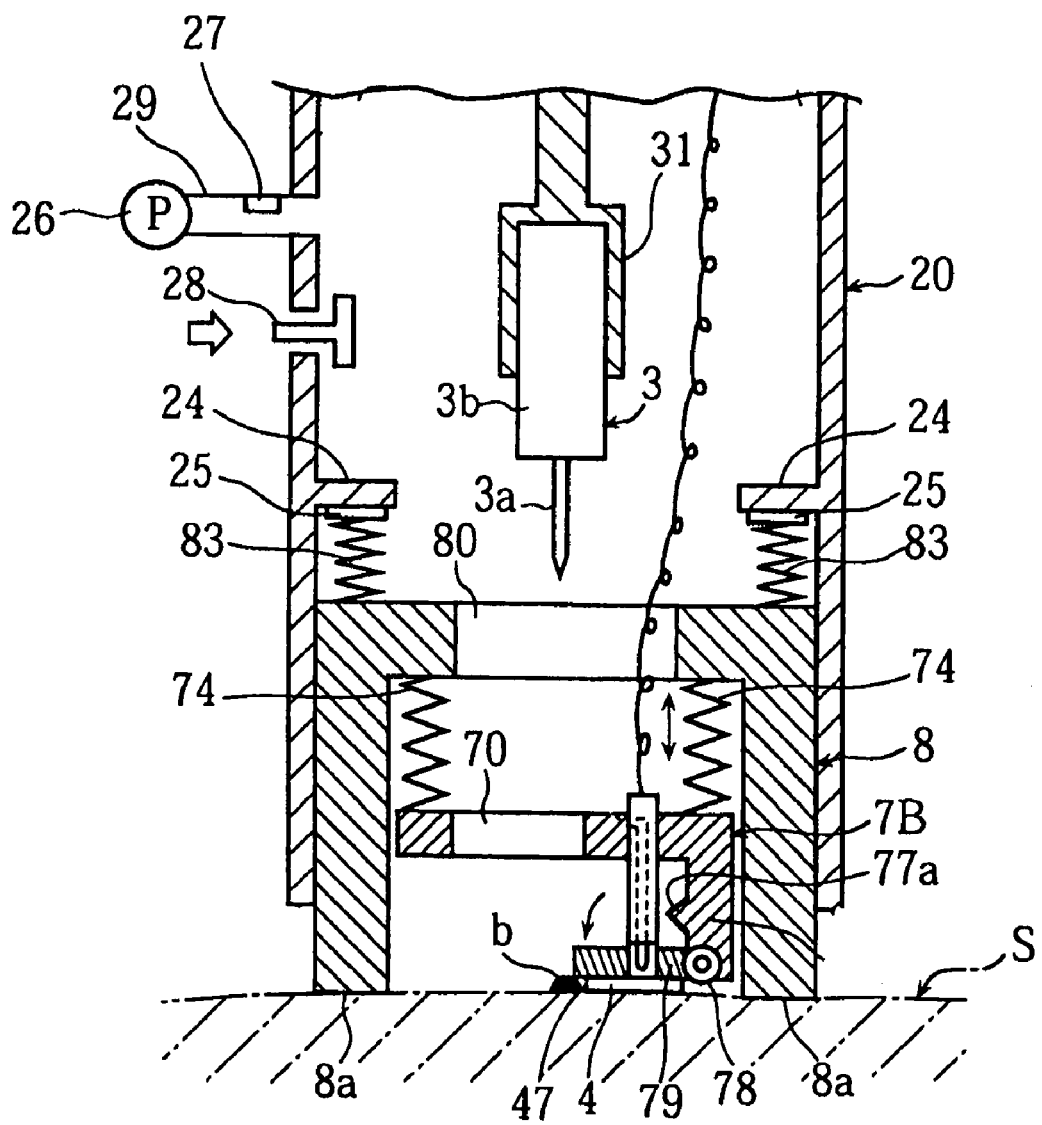
FIG. 20 is a sectional view illustrating a principal portion of another lancing apparatus according to the present invention.

The lancing apparatus shown in FIGS. 19 and 20 differs from that of the foregoing embodiment in that the analysis sensor 4 held by the sensor holder 7B can vary its inclination angle α. Specifically, the sensor holder 7B includes a pivot member 79 which is pivotable about a support shaft 78 axially of the cylindrical member 8. The analysis sensor 4 is attached to the pivot member 79 so that the inclination angle α of the analysis sensor 4 varies in accordance with the pivotal movement of the pivot member 79. Adjacent to the pivot member 79 of the sensor holder 7B is provided a stopper 77*a*. When the inclination angle α reaches a predetermined angle, the stopper engages the pivot member 79 to restrain the rotation of the pivot member 79 so that the inclination angle α does not exceed the predetermined angle.

With this structure, as shown in FIG. 19, when the skin S bulges due to depressurization of the cylindrical member 8, the skin S pushes up the pivot member 79 for pivoting, so that the inclination angle α of the analysis sensor 4 varies. The inclination angle α of the analysis sensor 4 varies depending on the degree of bulging of the skin S, whereby the analysis sensor 4 can be kept in close contact with the inclined surface of the bulging portion of the skin S. Therefore, similarly to the lancing apparatus A of the foregoing embodiment, in extracting blood b while bulging the skin S, the sample introducing portion 47 of the analysis sensor 4 can be kept close to the bleeding portion regardless of the variation of the bulging amount of the skin S. Therefore, the blood b can be properly guided to the sample introducing portion 47 of the analysis sensor 4. Since the inclination angle α is prevented from exceeding a predetermined value, the analysis sensor 4 does not rotate excessively to be spaced from the skin S even when the amount of bulging of the skin S is large.

As shown in FIG. 20, when negative pressure in the cylindrical member 8 is relieved after the skin S is lanced, the analysis sensor 4 and the pivot member 79 pivot downward by their own weight, following the shrinkage of the bulge of the skin S. Thus, when the skin S returns to a generally flat configuration, the analysis sensor 4 is not inclined. In this state, the sample introducing portion 47 is closer to the bleeding portion than when the analysis sensor 4 is inclined due to the bulging of the skin S. Therefore, this condition is further suitable for guiding much blood to the sample introducing portion 47. In the above structure, the pivotal movement of the pivot member 79 in the direction to reduce the inclination angle α may be produced by utilizing e.g. the resilient force of a spring, not by utilizing its own weight. In such a case, the analysis sensor 4 can follow the shrinkage of the bulge of the skin S even when the lancing apparatus is used in a horizontal posture or an inclined posture.

Figure 21:
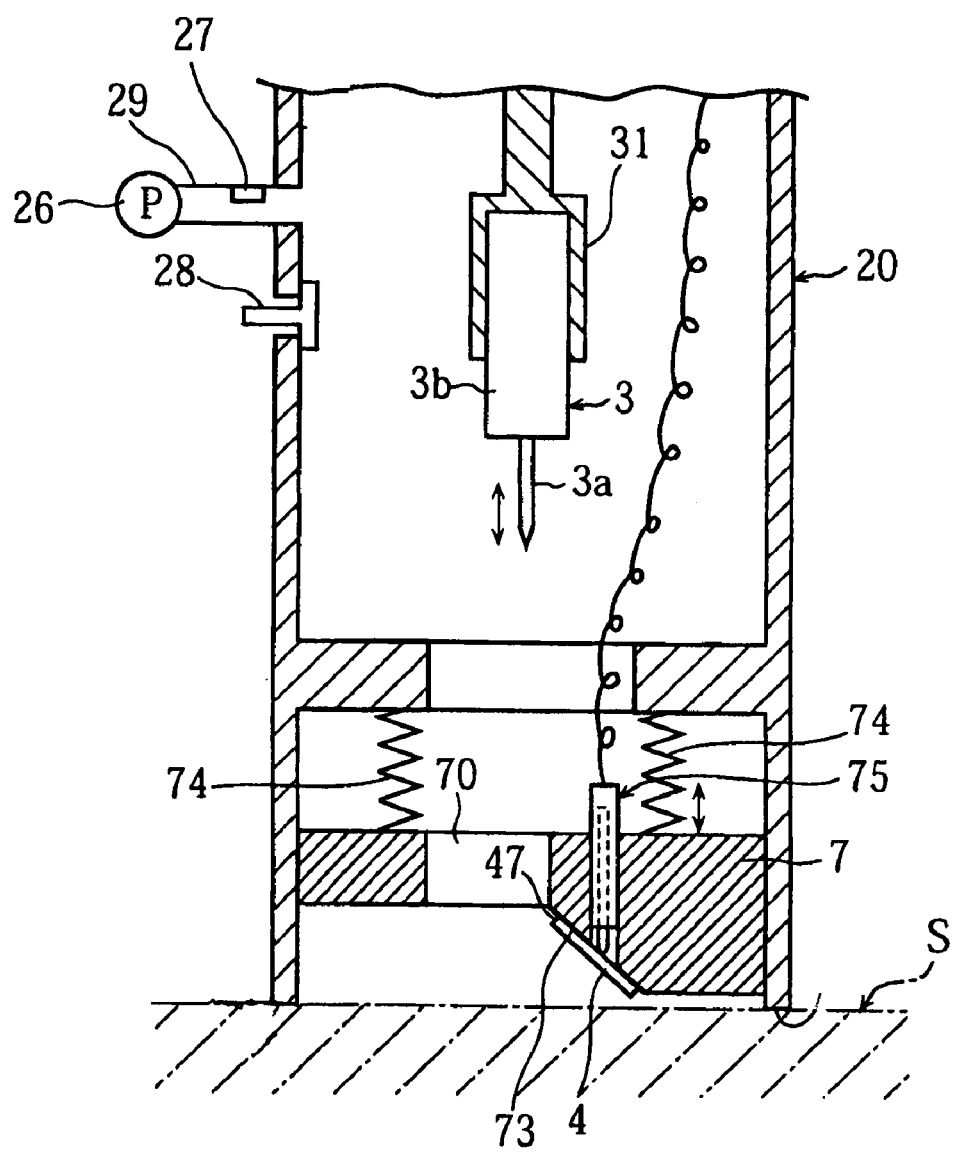
FIG. 21 is a sectional view illustrating a principal portion of another lancing apparatus according to the present invention.

The structure shown in FIG. 21 does not include a member corresponding to the cylindrical member 8 of the foregoing embodiments. In this embodiment, a sensor holder 7 holding an analysis sensor 4 is disposed in a cylindrical member 20 formed integrally on a housing 2 to be movable upward and downward via a spring 74.

In using the device having the above structure, the front end of the cylindrical member 20 is pressed against the skin S. When the skin S bulges due to negative pressure generated in the cylindrical member 20, the analysis sensor 4 and the sensor holder 7 are lifted against the resilient force of the spring 74. Thus, this structure again provides the advantages intended in the present invention. Since the lancing apparatus dispenses with a cylindrical member formed separately from the housing 2, the structure of the lancing apparatus can be simplified. In this way, the cylindrical member according to the present invention may be either integral with or separate from the housing.

Figure 22:
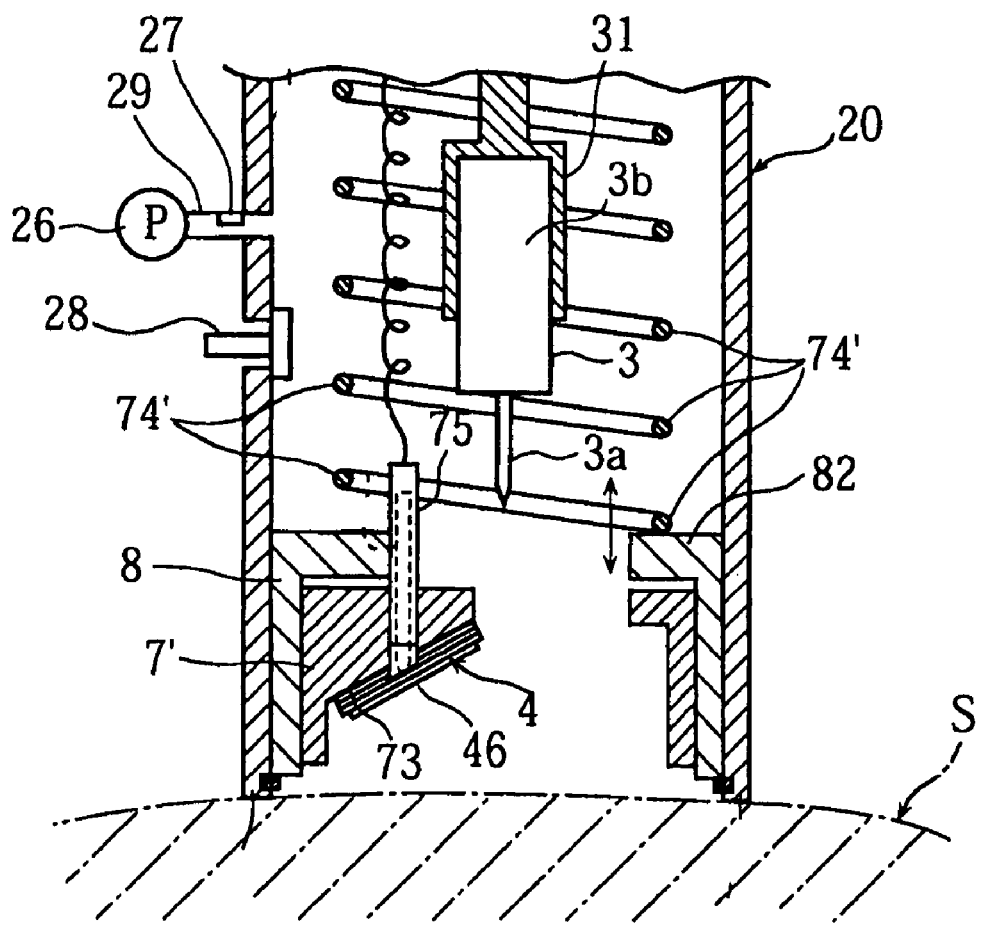
FIG. 22 is a sectional view illustrating a principal portion of another lancing apparatus according to the present invention.

In the structure shown in FIG. 22, the sensor holder 7' is fixedly mounted to the cylindrical member 8. The cylindrical member 8 is slidably fitted in the cylindrical member 20 of the housing 2 so as not to project downward from the cylindrical member 20 and is biased downward by a spring 74'.

With this structure again, the sensor holder 7' can move upward and downward in accordance with the up and down movement of the cylindrical member 8. Therefore, it is possible to make the sensor holder 7' move upward and downward following the bulging of the skin S.

The present invention is not limited to the above-described embodiments. The specific structure of each part of the lancing apparatus according to the present invention may be varied in various ways.

For example, the usage of the lancing apparatus according to the present invention is not limited to measurement of glucose concentration in blood. By changing the structure of the analysis component, the apparatus of the present invention can be used for various kinds of measurement or analysis other than that described above. The analysis component of the present invention need not necessarily include a reagent, but may only have the function for sampling blood. Although it is preferable that the lancing apparatus according to the present invention includes an analyer for analyzing a sample, the present invention is not limited thereto, and the lancing apparatus may not have the function for analyzing the sample extracted to the analysis component.

It is preferable that the negative pressure generator comprise an electrically driven pump. However, as the negative pressure generator, use may be alternatively made of a manual pump or a pump mechanism which generates negative pressure in the cylindrical member utilizing the advancing movement of the lancet. As means for moving the lancet, the resilient force of a resilient member may be utilized for the advancing movement, whereas the retreating movement may be performed manually. Alternatively, both of the advancing movement and the retreating movement may be performed utilizing the resilient force of a resilient member such as a spring.

The invention claimed is:

1. A lancing apparatus comprising:
a housing separately formed with a cylindrical member having an open front end for contact with skin, the cylindrical member further having a rear opening,
a lancet disposed in the housing and movable to advance in a first direction from a deeper portion in the housing behind the rear opening of the cylindrical member toward the front end of the cylindrical member through the rear opening of the cylindrical member, and
an analysis component disposed in the cylindrical member between the front end and the rear opening of the cylindrical member for contact with skin even before lancing the skin with the lancet;
wherein the analysis component is supported for movement relative to the cylindrical member separately from the lancet in a second direction opposite to the first direction upon receiving a force from the skin in the second direction while the analysis component keeps contact with the skin in a lancing operation;
wherein the cylindrical member is telescopically supported by the housing for movement relative to the housing in the second direction separately from the analysis component upon receiving a force from the skin in the lancing operation.

2. The lancing apparatus according to claim 1, further comprising a negative pressure generator for generating negative pressure in the cylindrical member.

3. The lancing apparatus according to claim 1, wherein the cylindrical member is mounted to the housing to partially project from the housing.

4. The lancing apparatus according to claim 1, further comprising a holder for holding the analysis component, the holder being supported by the cylindrical member via a resilient member capable of expanding and contracting in the first direction and the second direction.

5. The lancing apparatus according to claim 4, wherein the holder is arranged to engage the lancet advancing in the first direction to inhibit further advancement of the lancet.

6. The lancing apparatus according to claim 1, wherein the analysis component includes a surface oriented in the first direction for contacting the skin, the skin contacting surface being inclined to extend toward a deeper portion in the housing as the skin contacting surface extends closer to a central axis of the cylindrical member.

7. The lancing apparatus according to claim 6, wherein an inclination angle of the analysis component is variable.

8. The lancing apparatus according to claim 7, further comprising a stopper for preventing the analysis component from inclining more than a predetermined angle.

9. The lancing apparatus according to claim 6, wherein the skin contacting surface is adherent.

10. The lancing apparatus according to claim 1, wherein the analysis component comprises a substrate, a reagent layer disposed on the substrate, a sample introducing portion formed at an edge of the substrate, and a capillary for guiding sample liquid adhering to the sample introducing portion to the reagent layer.

11. The lancing apparatus according to claim 10, wherein the sample introducing portion is defined by a surface which is made of hydrophilic material.

12. A lancing apparatus comprising:
a housing separately formed with a cylindrical member having an open front end for contact with skin, the cylindrical member further having a rear opening,
a lancet disposed in the housing and movable to advance in a first direction from a deeper portion in the housing behind the rear opening of the cylindrical member toward the front end of the cylindrical member through the rear opening of the cylindrical member,
an analysis component disposed in the cylindrical member between the front end and the rear opening of the cylindrical member for contact with skin even before lancing the skin with the lancet;
a determiner for determining whether or not a sample is introduced to the analysis component,
a negative pressure generator for generating negative pressure in the cylindrical member, and
a controller to relieve the negative pressure generated in the cylindrical member when the determiner determines that the sample is not introduced to the analysis component within a predetermined time after the lancing apparatus is advanced toward the front end of the cylindrical member,
wherein the analysis component is supported for movement relative to the cylindrical member separately from the lancet in a second direction opposite to the first direction upon receiving a force from the skin in the second direction while the analysis component keeps contact with the skin in a lancing operation;
wherein the cylindrical member is telescopically supported by the housing for movement relative to the housing in the second direction separately from the analysis component upon receiving a force from the skin in the lancing operation.

13. The lancing apparatus according to claim 12, further comprising a relief valve for causing an inside of the cylindrical member to communicate with an outside of the housing,
wherein the controller is capable of opening the relief valve to relieve the negative pressure in the cylindrical member.

14. The lancing apparatus according to claim 12, wherein the controller controls the negative pressure generator to regenerate negative pressure in the cylindrical member after negative pressure previously generated in the cylindrical member is relieved.

15. The lancing apparatus according to claim 14,
wherein the advancing movement of the lancet is performed repetitively under control of the controller, and
wherein the lancet advances again under control of the controller when the determiner determines that the sample is not introduced to the analysis component within a predetermined time after negative pressure is regenerated in the cylindrical member.

16. The lancing apparatus according to claim 12, wherein the controller controls the negative pressure generator to further lower a pressure in the cylindrical member after the lancet is advanced and before the negative pressure previously generated in the cylindrical member is relieved.

17. The lancing apparatus according to claim 12, further comprising an analyzer for analyzing the sample introduced to the analysis component and a notifier for notifying analysis results provided by the analyzer.

18. The lancing apparatus according to claim 17, wherein the controller causes the notifier to give a notice when the analysis of the sample by the analyzer is not performed within a predetermined time after the lancet is advanced.

19. The lancing apparatus according to claim 17, further comprising a detector for detecting a pressing force applied to the cylindrical member in a direction opposite to the advancing direction of the lancet, wherein the notifier gives a notice when the pressing force detected by the detector exceeds a predetermined value.

20. A lancing apparatus comprising:
a housing separately formed with a cylindrical member having an open front end for contact with skin,
a lancet disposed in the housing and movable to advance in a first direction from a deeper portion in the housing toward the front end of the cylindrical member for lancing skin, and
an analysis component supported on a holder in the cylindrical member ahead of the lancet in the first direction, the holder having a lancet passing hole, the lancet in a non-lancing position being located behind the lancet passing hole of the holder, the lancet advancing through the lancet passing hole of the holder for lancing the skin,
wherein the analysis component is supported for movement together with the holder relative to the cylindrical member separately from the lancet in a second direction opposite to the first direction upon receiving a force from the skin in the second direction for following bulging of the skin in a lancing operation;
wherein the cylindrical member is telescopically supported by the housing for movement relative to the housing in the second direction separately from the analysis component upon receiving a force from the skin in the lancing operation.

21. A lancing apparatus comprising:
a housing;
a cylindrical member slidably fitted in the housing and having an open front end for contact with skin, the cylindrical member further having a rear opening,
a lancet disposed in the housing and movable to advance in a first direction from a deeper portion in the housing behind the rear opening of the cylindrical member toward the front end of the cylindrical member through the rear opening of the cylindrical member, and
an analysis component disposed in the cylindrical member between the front end and the rear opening of the cylindrical member for contact with skin even before lancing the skin with the lancet;
wherein the analysis component is supported for movement relative to the cylindrical member separately from the lancet in a second direction opposite to the first direction upon receiving a force from the skin in the second direction while the analysis component keeps contact with the skin in a lancing operation;
wherein the cylindrical member is configured to telescopically slide relative to the housing in the second direction separately from the analysis component upon receiving a force from the skin in the lancing operation.

* * * * *